US010327869B2

(12) United States Patent
Suttin et al.

(10) Patent No.: US 10,327,869 B2
(45) Date of Patent: Jun. 25, 2019

(54) ATTACHMENT MEMBERS WITH INTERNALLY LOCATED RADIOPAQUE INFORMATION MARKERS FOR CT SCAN

(71) Applicant: BIOMET 3I, LLC, Palm Beach Gardens, FL (US)

(72) Inventors: Zachary B Suttin, West Palm Beach, FL (US); Stephen S. Porter, West Palm Beach, FL (US)

(73) Assignee: Biomet 3I, LLC, Palm Beach Gardens, FL (US)

(*) Notice: Subject to any disclaimer, the term of this patent is extended or adjusted under 35 U.S.C. 154(b) by 89 days.

(21) Appl. No.: 15/299,074

(22) Filed: Oct. 20, 2016

(65) Prior Publication Data
US 2017/0112598 A1 Apr. 27, 2017

Related U.S. Application Data

(60) Provisional application No. 62/244,548, filed on Oct. 21, 2015.

(51) Int. Cl.
*A61C 8/00* (2006.01)
*A61C 13/00* (2006.01)
(Continued)

(52) U.S. Cl.
CPC .......... *A61C 8/0001* (2013.01); *A61C 8/005* (2013.01); *A61C 8/006* (2013.01);
(Continued)

(58) Field of Classification Search
CPC ........................ A61C 2201/005; A61C 8/0001; A61C 8/005; A61C 8/0068; A61C 8/006;
(Continued)

(56) References Cited

U.S. PATENT DOCUMENTS 6,333,971 B2 * 12/2001 McCrory ........... A61K 49/0409
378/162
2002/0039717 A1 * 4/2002 Amber ................. A61C 8/0001
433/172
(Continued)

FOREIGN PATENT DOCUMENTS

JP 2013202256 A 10/2013
WO WO-2017070358 A1 4/2017

OTHER PUBLICATIONS

"International Application Serial No. PCT/US2016/057931, International Search Report dated Dec. 14, 2016", 5 pgs.
(Continued)

*Primary Examiner* — Wade Miles
*Assistant Examiner* — Shannel N Wright
(74) *Attorney, Agent, or Firm* — Schwegman Lundberg & Woessner, P.A.

(57) ABSTRACT

An attachment member for mating with a dental implant includes a non-rotational structure and a body. The non-rotational structure is configured to mate with a corresponding non-rotational feature of the dental implant. The body extends from the non-rotational structure. The body has (i) an exterior side surface configured to at least partially engage gingival tissue adjacent to the dental implant, (ii) an exterior top surface that is exposed through the gingival tissue, (iii) a screw access bore for receiving a screw that attaches the attachment member to the dental implant in a removable fashion, and (iv) a set of radiopaque information markers that is located internal to the exterior side surface and the exterior top surface. The set of radiopaque information markers indicates information regarding the dental implant that is revealed in response to a scan from a computerized tomography (CT) scanner.

13 Claims, 17 Drawing Sheets

(51) Int. Cl.
*A61C 13/34* (2006.01)
*A61B 6/03* (2006.01)
*A61B 6/14* (2006.01)
*A61B 90/00* (2016.01)
*A61C 9/00* (2006.01)

(52) U.S. Cl.
CPC .......... *A61C 13/0004* (2013.01); *A61C 13/34* (2013.01); *A61B 6/032* (2013.01); *A61B 6/14* (2013.01); *A61B 2090/3916* (2016.02); *A61B 2090/3966* (2016.02); *A61C 8/008* (2013.01); *A61C 8/0068* (2013.01); *A61C 9/004* (2013.01); *A61C 2201/005* (2013.01)

(58) Field of Classification Search
CPC ................ A61C 13/0004; A61C 13/34; A61C 2201/0056; A61C 9/004; A61C 9/0046; A61B 6/032; A61B 6/14; A61B 2090/3916; A61B 2090/3966; A61B 90/39
USPC ............................................ 433/215, 75, 173
See application file for complete search history.

(56) References Cited

U.S. PATENT DOCUMENTS

| | | | |
|---|---|---|---|
| 2006/0019219 A1* | 1/2006 | Saliger | A61C 8/00 433/173 |
| 2007/0141531 A1* | 6/2007 | De Clerk | A61C 8/0001 433/173 |
| 2008/0176188 A1* | 7/2008 | Holzner | A61C 8/0001 433/215 |
| 2010/0296710 A1* | 11/2010 | Schneider | A61C 8/0001 382/128 |
| 2011/0129792 A1 | 6/2011 | Berckmans, III et al. | |
| 2014/0080095 A1* | 3/2014 | Suttin | A61C 13/34 433/202.1 |
| 2014/0205969 A1* | 7/2014 | Marlin | A61C 8/0001 433/173 |
| 2014/0297232 A1* | 10/2014 | Miyoshi | G06F 17/50 703/1 |
| 2014/0319713 A1 | 10/2014 | Blaisdell et al. | |
| 2015/0230895 A1* | 8/2015 | Soler Cegarra | A61C 9/004 433/173 |

OTHER PUBLICATIONS

"International Application Serial No. PCT/US2016/057931, Written Opinion dated Dec. 14, 2016", 6 pgs.

* cited by examiner

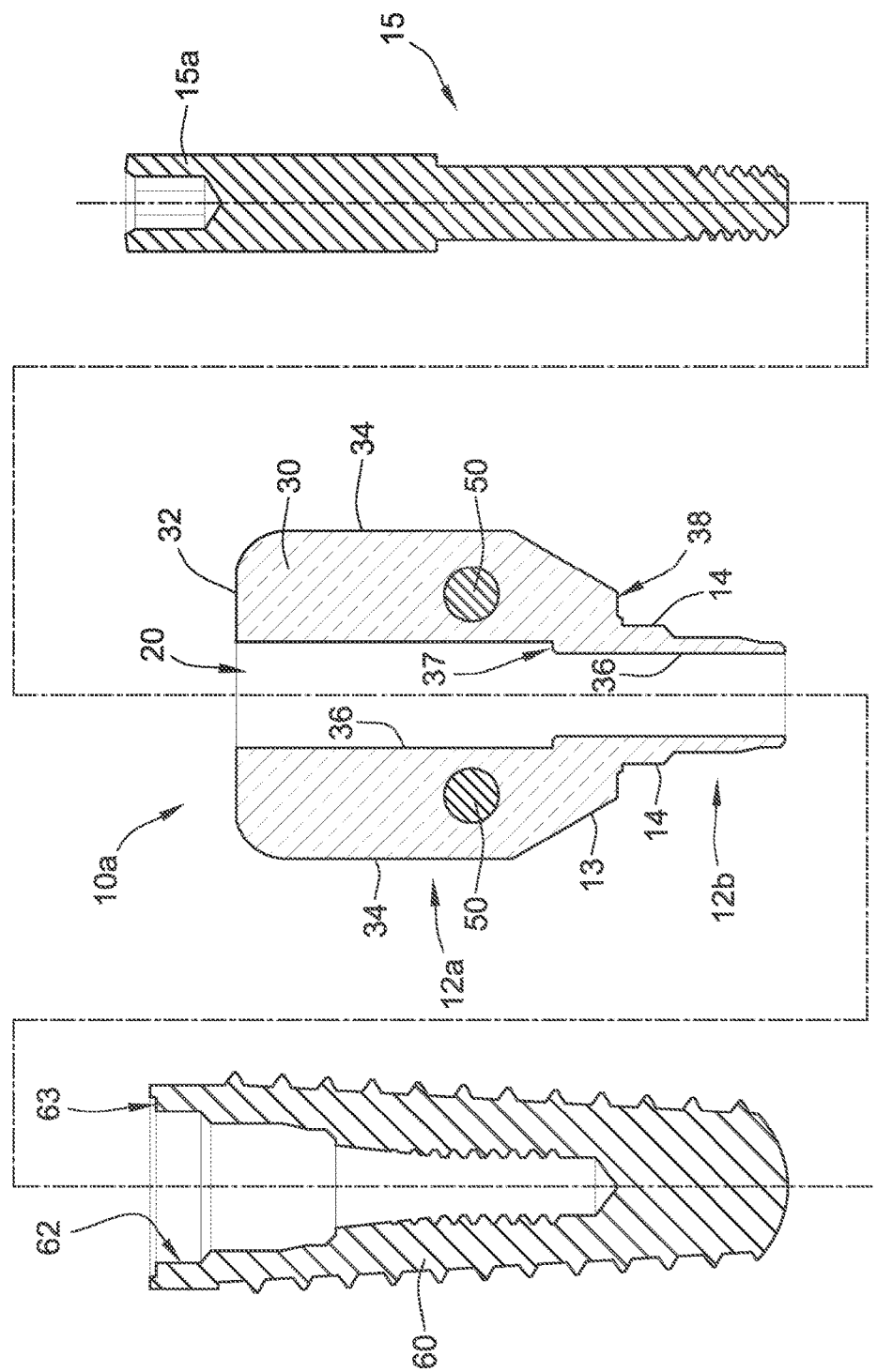

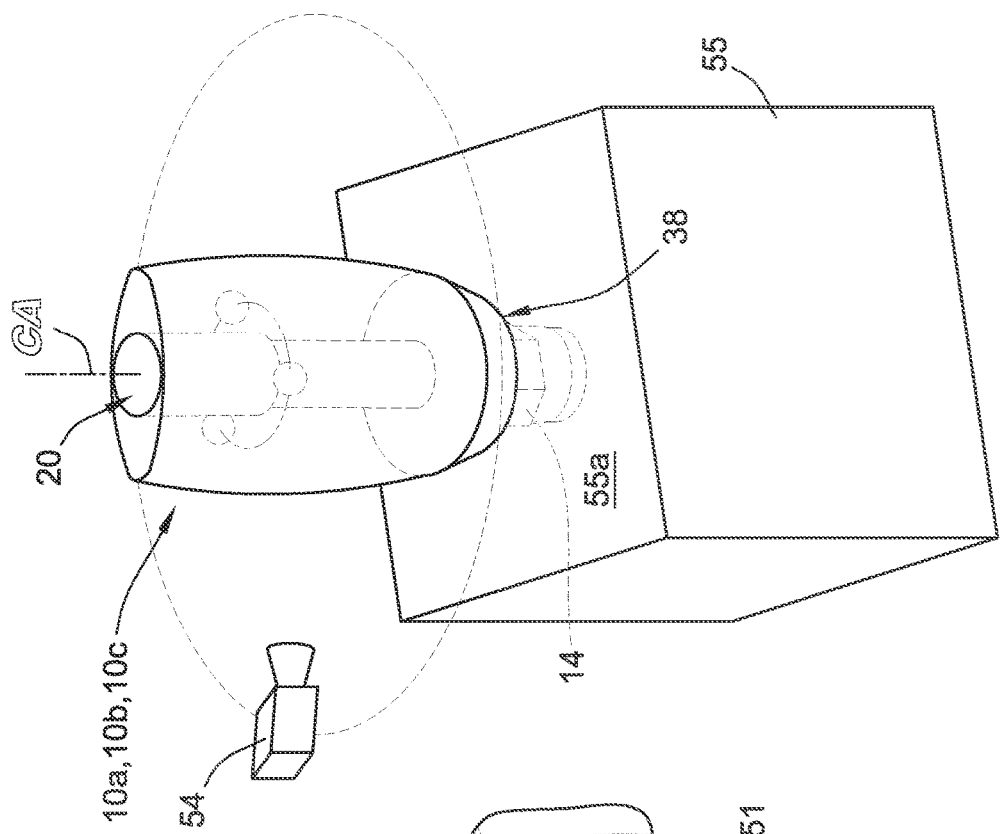
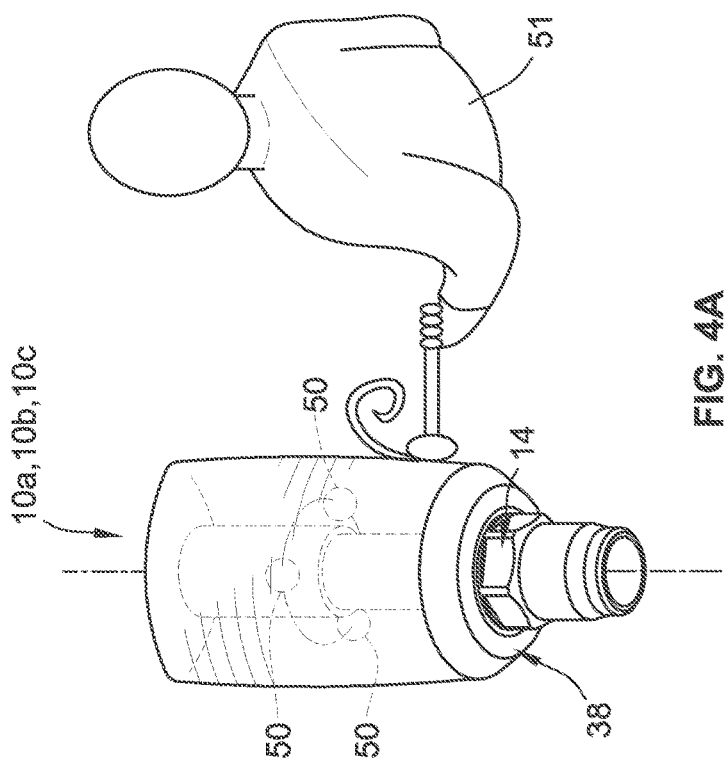
FIG. 4A
FIG. 4B

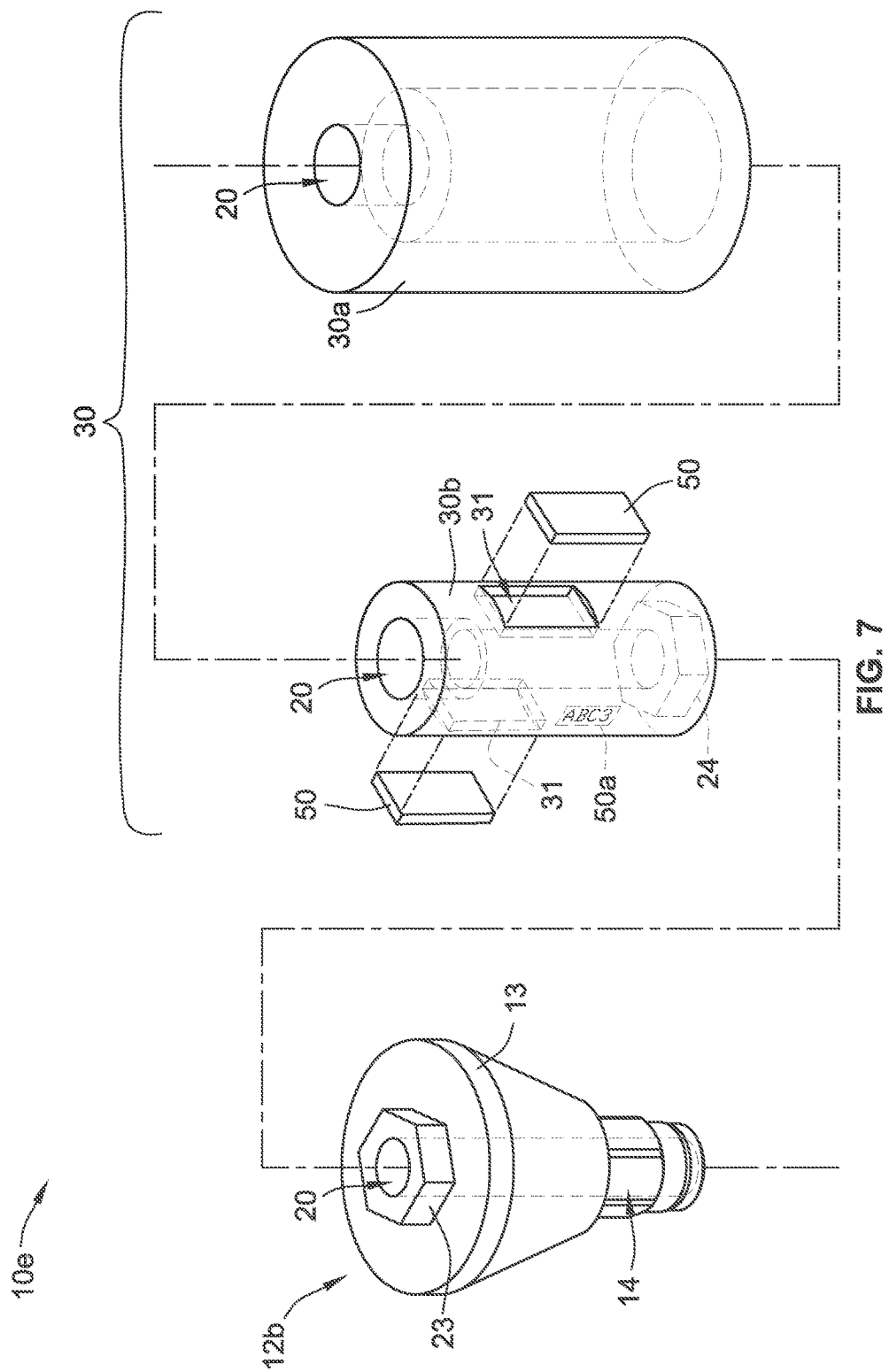

ATTACHMENT MEMBERS WITH INTERNALLY LOCATED RADIOPAQUE INFORMATION MARKERS FOR CT SCAN

CLAIM OF PRIORITY

This application claims the benefit of U.S. Provisional Patent Application Ser. No. 62/244,548, filed on Oct. 21, 2015, the benefit of priority of which is claimed hereby, and which is incorporated by reference herein in its entirety.

FIELD OF THE INVENTION

The present disclosure relates generally to attachment members with internally located radiopaque information markers. More particularly, the present disclosure relates to CT scanning attachment members with internally located radiopaque information markers for use in developing a final dental prosthesis.

BACKGROUND OF THE INVENTION

The dental restoration of a partially or wholly edentulous patient with artificial dentition is typically done in two stages. In the first stage, an incision is made through the gingiva to expose the underlying bone. An artificial tooth root, in the form of a dental implant, is placed in the jawbone for osseointegration. The dental implant generally includes a threaded bore to receive a retaining screw for holding mating components thereon. During the first stage, the gum tissue overlying the implant is sutured and heals as the osseointegration process continues.

Once the osseointegration process is complete, the second stage is initiated. Here, the gingival tissue is re-opened to expose an end of the dental implant. A healing component or healing abutment is fastened to the exposed end of the dental implant to allow the gingival tissue to heal therearound. It should be noted that, in some situations, the healing abutment can be placed on the dental implant immediately after the implant has been installed and before osseointegration, thereby combining the osseointegration step and gingival healing step into a one-step process.

Some prior healing abutments were generally round in profile, but the artificial teeth or prostheses that eventually replaced the healing abutments were not. Thus, the gingival tissue would heal around the healing abutments creating a gingival emergence profile that approximated the size and contour of the healing abutment and not necessarily the size and contour of the final prosthesis that was eventually attached to the implant. The resulting discrepancies between the emergence profile of the patient's gingiva and the installed final prosthesis could sometimes require additional visits with the dentist or clinician to finalize the installation process and/or compromise the aesthetic outcome of the installed final prosthesis (e.g., the visual look of the patient's gingival tissue abutting the final prosthesis). Thus, in some instances in more recent years, standard healing abutments have been replaced with temporary prosthetic abutments.

Further, implant dentistry restorative methods have advanced beyond requiring a fixture-level (e.g., dental implant level) impression as the starting point for developing a final dental prosthesis. In some such cases pre-defined scan members (e.g., Encode® Healing Abutments available from Biomet 3i, LLC) are assembled to the dental implants during the gingival healing stage. The pre-defined scan members include visually scannable features (e.g., markers) that, when scanned using an intraoral scanner (IOS) and subsequently interpreted, provide information about the location and orientation of the underlying dental implant that is used in developing the final dental prosthesis.

However, these prior pre-defined scan members only include the visually scannable features on an exposed top occlusal surface of the scan members. Such a placement of the scannable features is required such that the scannable features could be visualized (i.e., picked-up) by the IOS scanner with the scan members attached to the dental implant in the mouth of the patient. Thus, the exposed top occlusal surface may have geometric limitations such that the exposed top occlusal surface was suitable for including the visually scannable features in a manner that readily allowed the visually scannable features to be picked-up in a scan and interpreted. And some pre-defined scan members may be installed in a patient's mouth during the healing period (e.g., for several months) such that the pre-defined scan members (especially their exposed occlusal surface that includes the scannable features) are subjected to wear and tear due to standard mastication, which could alter the scannable features and impact accuracy of future scans of the pre-defined scan members.

Although such methods using pre-defined scan members provide many benefits (e.g., improved aesthetics, reduced complexity, and potentially accelerated treatment times), such methods are reliant on intraoral scanning technology that must directly visualize an exposed surface with exposed visually scannable features thereon. A need exists for a restorative solution that does not require pre-defined scan members with visually scannable features thereon as to further improve restorative flexibility. The present disclosure is directed to solving these problems and addressing other needs.

SUMMARY OF THE INVENTION

The present disclosure is directed towards attachment members (e.g., scan bodies, scan members, abutments, caps, patient-specific temporary prostheses, pre-defined non-patient specific scan members, etc.) that couple with a dental implant installed in a patient's mouth. The attachment members can have non-custom standard shapes (e.g., cylindrical, oval, etc.), non-custom standard anatomical shapes (e.g., tooth shape), and/or customized anatomical shapes tooth shape), or a combination thereof. The attachment members of the present disclosure are different from prior scan members in that the scannable features of the attachment members of the present disclosure are not positioned on an exposed top occlusal surface thereof to be visually scanned using an intraoral scanner. Rather, the attachment members of the present disclosure include a set of radiopaque information markers that is located internal to an exterior side surface and the exterior top occlusal surface of the attachment member such that the set of radiopaque information markers is completely internal to the body of the attachment member and not visible. As the set of radiopaque information markers is not visible, the attachment members of the present disclosure are not visually scanned or picked-up using a IOS scanner, but rather the set of radiopaque information markers is scanned and picked-up using a computerized tomography (CT) scanner (e.g., a cone beam CT scanner traditionally used in dental applications). The CT scanners generate CT scan data that is processed by one or more computers using software that is able to segment the radiopaque information markers from the rest of the scan, resulting in information markers that provide one or more pieces of information about the attachment member itself and/or one or more pieces of information about the dental implant to which the attachment member is coupled. Further, additional features (e.g., exterior surfaces of the attachment member, exterior surfaces of gingival tissue, adjacent teeth, jaw bone, etc.) can be segmented from the CT scan data for use in designing and/or fabricating one or more components (custom abutment, crown, etc.).

In one implementation, an attachment member for mating with a dental implant includes a non-rotational structure and a body. The non-rotational structure is configured to mate with a corresponding non-rotational feature of the dental implant. The body extends from the non-rotational structure. The body has (i) an exterior side surface configured to at least partially engage gingival tissue adjacent to the dental implant, (ii) an exterior top surface that is exposed through the gingival tissue, (iii) a screw access bore for receiving a screw that attaches the attachment member to the dental implant in a removable fashion, and (iv) a set of radiopaque information markers that is located internal to the exterior side surface and the exterior top surface. The set of radiopaque information markers indicates information regarding the dental implant that is revealed in response to a scan from a computerized tomography (CT) scanner.

In another implementations, an attachment member for mating with a dental implant includes a non-rotational structure and a body. The non-rotational structure is configured to mate with a corresponding non-rotational feature of the dental implant. The body extends from the non-rotational structure. The body has a set of internally located radiopaque information markers that are not visible from an exterior surface of the attachment member. The set of radiopaque information markers indicates a relative position of an upper surface of the dental implant and an orientation of the corresponding non-rotational feature of the dental implant.

In yet a further implementation, the present disclosure involves a method of creating a custom abutment for attachment to a dental implant in a mouth of a patient includes by use of a computerized tomography (CT) scanner, scanning the mouth to generate CT scan data associated with at least teeth, gingival tissue, and an attachment member coupled to the dental implant. The attachment member has a set of internally located radiopaque information markers that are not visible from an exterior surface of the attachment member. The set of radiopaque information markers indicates information regarding the dental implant. Based on the CT scan data, a three-dimensional model of at least a portion of the mouth including at least a portion of the dental implant as indicated by the information from the set of radiopaque information markers is displayed on a display device.

In another implementation, the present disclosure involves a method of manufacturing a permanent prosthesis for attachment to a dental implant installed in a mouth of a patient includes fabricating a patient specific temporary prosthesis (PSTP). The PSTP has (i) a non-rotational structure configured to mate with a corresponding non-rotational feature of the dental implant and (ii) a body extending from the non-rotational structure. The body has a set of radiopaque information markers located internal to an exterior surface of the attachment member. The set of radiopaque information markers indicates a relative position of an upper surface of the dental implant and an orientation of the corresponding non-rotational feature of the dental implant. A supragingival portion of the PSTP has an anatomical tooth shape. By use of a computerized tomography (CT) scanner, the method includes scanning, outside of the mouth of the patient, the PSTP to obtain first CT scan data. The PSTP is attached to the dental implant in the mouth of the patient. Gingival tissue surrounding the PSTP is permitted to heal in the mouth of the patient. By use of the CT scanner, the method includes scanning the mouth of the patient including the PSTP therein to obtain second CT scan data. The permanent prosthesis is manufactured using at least the obtained second CT scan data.

Additional aspects of the present disclosure will be apparent to those of ordinary skill in the art in view of the detailed description of various implementations, which is made with reference to the drawings, a brief description of which is provided below.

BRIEF DESCRIPTION OF THE DRAWINGS

The foregoing and other advantages of the disclosure will become apparent upon reading the following detailed description and upon reference to the drawings.

FIG. 1B is an exploded cross-sectional front view of the attachment member of FIG. 1A relative to a dental implant and a screw;

FIG. 4A is a perspective view depicting a clinician manually customizing/modifying a generally anatomically shaped attachment member having internal radiopaque information markers according to some aspects of the present disclosure;

FIG. 4B is a perspective view of the generally anatomically shaped attachment member of FIG. 4A non-rotationally coupled to a fixture and being scanned by a CT scanner according to some aspects of the present disclosure;

FIG. 7 is an exploded perspective view of an attachment member illustrating another method of positioning radiopaque information markers internal to a body of the attachment member during fabrication of the same according to some aspects of the present disclosure;

Figure 1A:
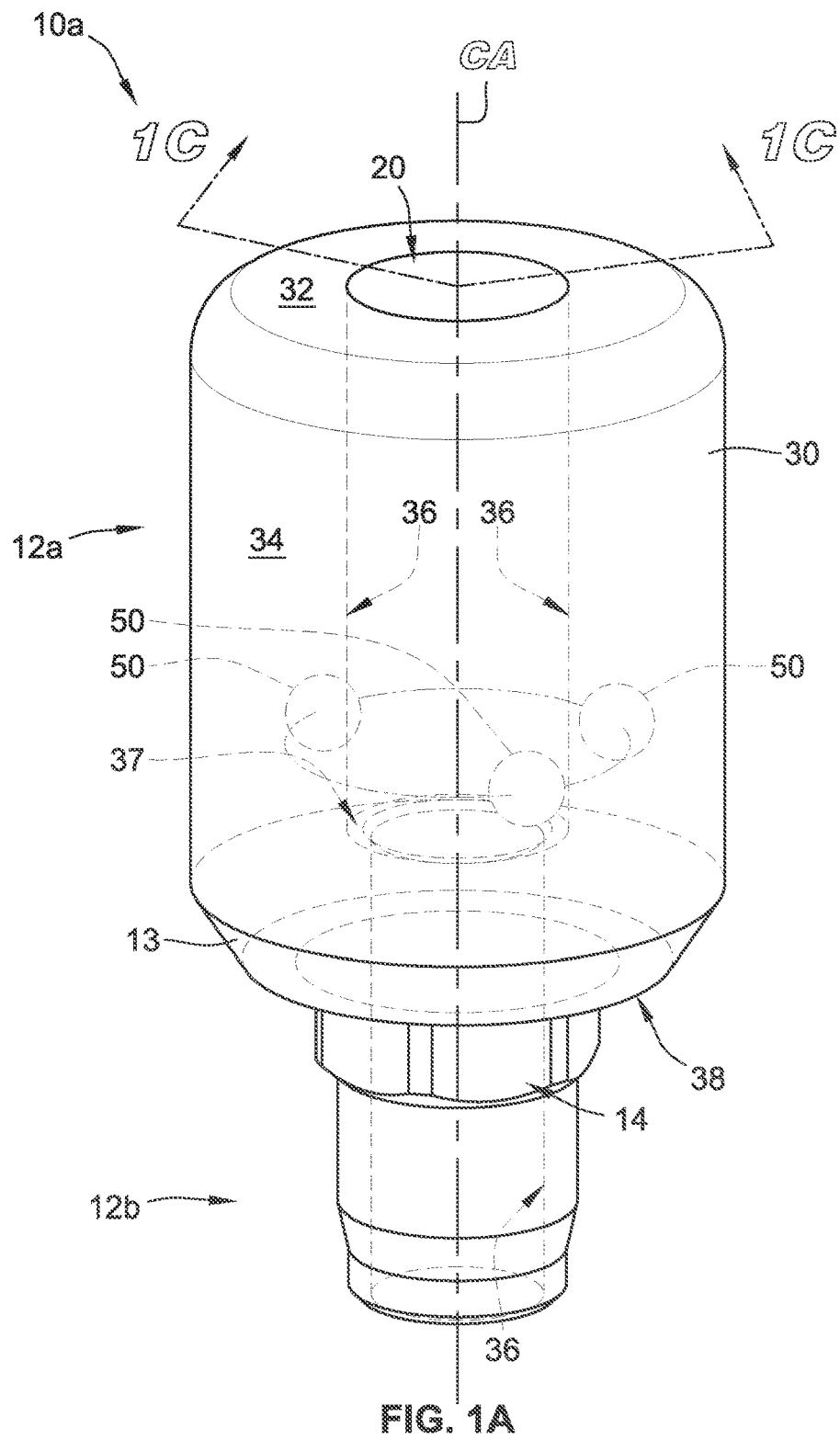
FIG. 1A is a perspective view of a generally cylindrical attachment member having internal radiopaque information markers according to some aspects of the present disclosure.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DESCRIPTION OF ILLUSTRATIVE EMBODIMENTS

Figure 1C:
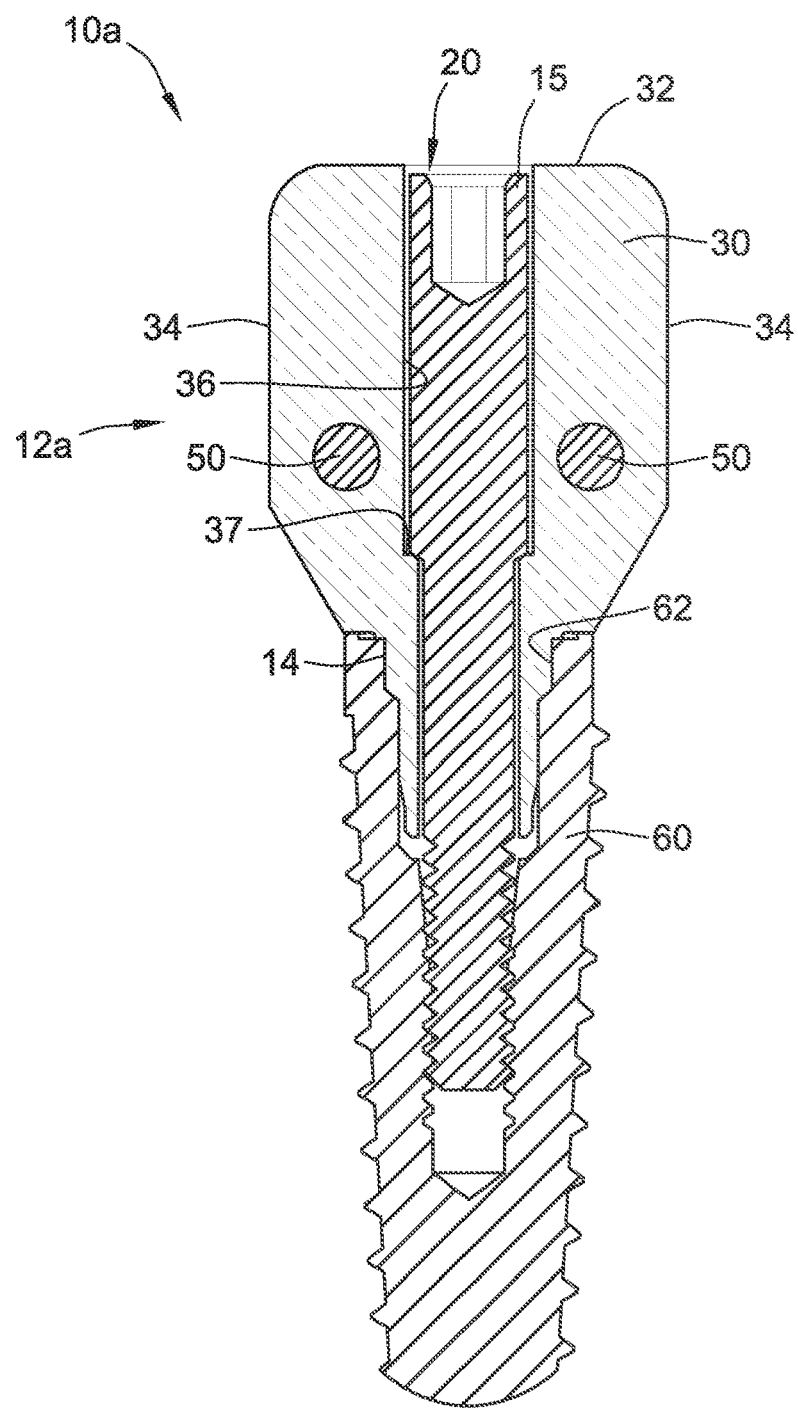
FIG. 1C is an assembled cross-sectional front view of the attachment member, the dental implant, and the screw of FIG. 1B.

Referring to FIGS. 1A-1C, an attachment member 10a is illustrated that is used to develop final or permanent patient-specific prostheses in accordance with the present disclosure. Further, the attachment member 10a can serve as a gingival healing abutment. The attachment member 10a has an upper or supragingival region 12a and a lower or subgingival region 12b, which are separated by a transition section 13, although the transition section 13 may be integral and included with the supragingival region 12a or the subgingival region 12b. Any portion of the transition section 13 and/or of the supragingival region 12a can be placed subgingival (e.g., below the gingival tissue) for a given installation. Similarly, any portion of the transition section 13 and/or of the subgingival region 12b can be placed supragingival (e.g., above the gingival tissue) for a given installation. Moreover, the supragingival region 12a can be referred to as a post region that is partially subgingival and/or partially supragingival.

The subgingival region 12b includes a non-rotational structure 14 (e.g., a hexagonal boss section) for mating with a corresponding non-rotational structure 62 (FIG. 1B) of a dental implant 60 (FIGS. 1B and 1C). The attachment member 10a can be removably held onto the dental implant 60 using a retaining screw 15 (as shown in FIG. 1C). The non-rotational structure 14 of the attachment member 10a can be any type of boss (e.g., polygonal boss, starshaped boss, clover-shaped boss, etc.) or socket (e.g., polygonal socket, star-shaped socket, clover-shaped socket, etc.) such that it corresponds with the non-rotational structure 62 of the underlying dental implant 60 to prevent relative rotation of the attachment member 10a with respect to the dental implant 60. It is contemplated that the attachment member 10a (and the other attachment members of the present disclosure) can be fashioned from gold, titanium, plastic, ceramic, acrylic, porcelain, or other similar metals and/or composites, or any combination thereof.

The supragingival region 12a is generally formed by a body 30 having a top occlusal surface 32 and an exterior side surface 34. The body 30 generally extends between the top occlusal surface 32 and the transition section 13 and/or the non-rotational structure 14 of the subgingival portion 12b of the attachment member 10a. The attachment member 10a further includes a screw access bore 20 (FIGS. 1A and 1B) that extends from the top occlusal surface 32, through the body 30 and through the subgingival portion 12b such that the screw 15 can be inserted therein to hold the attachment member 10a onto the dental implant 60 (FIG. 1C). The screw access bore 20 is formed by an inner surface 36 of the attachment member 10a that includes a shoulder 37 upon which a head 15a of the screw 15 engages/rests to couple the attachment member 10a with the dental implant 60 (as shown in FIG. 1C).

The attachment member 10a includes a set of radiopaque information markers 50 positioned internal to the body 30. Specifically, the set of radiopaque information markers 50 is positioned between the exterior side surface 34 of the body and the inner surface 36 of the attachment member 10a and between the top occlusal surface 32 of the body 30 and the non-rotational structure 14 of the subgingival portion 12b. As such, the set of radiopaque information markers 50 is not visible (e.g., visually viewable by a human) when looking at the attachment member 10a or when scanning the attachment member 10a using an intraoral scanner (not shown) that only visually scans exterior surfaces of objects.

The set of radiopaque information markers 50 is formed from a radiopaque material that is different from the material of the rest of the body 30. As such, when the attachment member 10a is scanned using a CT scanner (e.g., CBCT scanner), the set of radiopaque information markers 50 is distinguishable from and can be virtually/digitally segmented from the rest of the body 30 as described in further detail herein. Alternatively, the radiopaque information markers 50 can be made from the same material as the rest of the body, but the radiopaque information markers 50 are modified such that the radiopaque information markers 50 are distinguishable from and can be virtually/digitally segmented from the rest of the body 30. For example, the radiopaque information markers 50 may be coated with a radiopaque wash that distinguishes the radiopaque information markers 50 from the rest of the body 30. For another example, the radiopaque information markers 50 start out as the same material as the rest of the body, but then the material used to create the radiopaque information markers 50 is altered such that the radiopaque information markers 50 yield a different opacity. Altering the material can include, for example, compressing the material used to make the radiopaque information markers 50 such that the radiopaque information markers 50 are denser than the rest of the body 30, etc.

As shown in FIGS. 1A-1C, the set of radiopaque information markers 50 includes three radiopaque information markers 50 that have a generally spherical shape, although various other shapes of radiopaque information markers are contemplated herein, for example, as shown and described relative to FIGS. 8A-8G. Further each of the radiopaque information markers in the set of radiopaque information markers 50 is the same size (e.g., same diameter), although various other sizes and combination of shapes and sizes of radiopaque information markers are contemplated herein, for example, as shown and described relative to FIGS. 8A-8G.

The set of radiopaque information markers 50 is positioned within the body 30 in a predefined manner such that identification of the radiopaque information markers 50 indicates information about the attachment member 10a and/or about the dental implant 60 to which the attachment member 10a is coupled. For example, the radiopaque information markers 50 can indicate information such as, for example, (i) a location of a central axis CA of the attachment member 10a, (ii) a location of a central axis of the dental implant 60, (iii) a location of a seating surface 38 of the attachment member 10a, (iv) a diameter of the attachment member 10a, (v) a height of the attachment member 10a, (vi) a location of a table 63 of the implant 60, (vii) a location of one or more flats of the non-rotational structure 14 of the attachment member 10a, (viii) a location of one or more flats of the non-rotational structure 62 of the implant 60, (ix) a manufacturer of the dental implant 60, and/or (x) a connection type of the dental implant 60, etc.

As best shown in FIG. 1A, the set of radiopaque information markers 50 is positioned around the central axis CA of the screw access bore 20 such that each of the three radiopaque information markers 50 is positioned equidistantly from the central axis CA of the screw axis bore 20 (although various other spacing is contemplated). As such, identification of the radiopaque information markers 50 (e.g., by CT scanning the attachment member 10a and segmenting the radiopaque information markers 50 from the rest of the body) identifies the central axis CA (e.g., relative to other structures such as adjacent teeth in the patient's mouth, etc.), which is used in developing permanent and/or patient specific components (e.g., custom abutment, custom crown, etc.).

Further, the set of radiopaque information markers 50 (FIG. 1A) is positioned around the central axis CA of the screw access bore 20 such that one or more of the radiopaque information markers 50 corresponds with and/or otherwise identifies a rotational orientation of the non-rotational structure 14 of the attachment member 10a. For example, a center of each radiopaque information markers 50 can be located directly above a corner or intersection of two flats of the non-rotational structure 14. For another example, a center of each radiopaque information markers 50 can be located directly above a center line of a flat of the non-rotational structure 14. For yet another example, a plane including a center of a first radiopaque information markers 50 and also being equidistantly located from the other two radiopaque information markers 50 can be parallel and/or coincident with a plane including a flat of the non-rotational structure 14.

Further, the set of radiopaque information markers 50 (FIG. 1A) is positioned around the central axis CA of the screw access bore 20 such that one or more of the radiopaque information markers 50 corresponds with and/or otherwise identifies a location of the seating surface 38 of the attachment member 10a and/or a location of the table 63 of the dental implant 60. For example, a center of each radiopaque information markers 50 can be located in a plane that is parallel to a plane including the seating surface 38 of the attachment member 10a and/or the table 63 of the implant 60, where the plane is positioned at a predetermined known distance thereto (e.g., 2 millimeters above, 3 millimeters above, 4 millimeters above, 5 millimeters above, 10 millimeters above, etc.).

While some of the implementations and examples refer to a center of a radiopaque information marker, any other point or portion of the radiopaque information markers 50 can be used. For example, a lowest most point of the radiopaque information marker 50, a highest most point of the radiopaque information marker 50, an inner most point of the radiopaque information marker 50, and/or an outer most point of the radiopaque information marker 50, can be an identifying point, edge, or surface.

Figure 6:
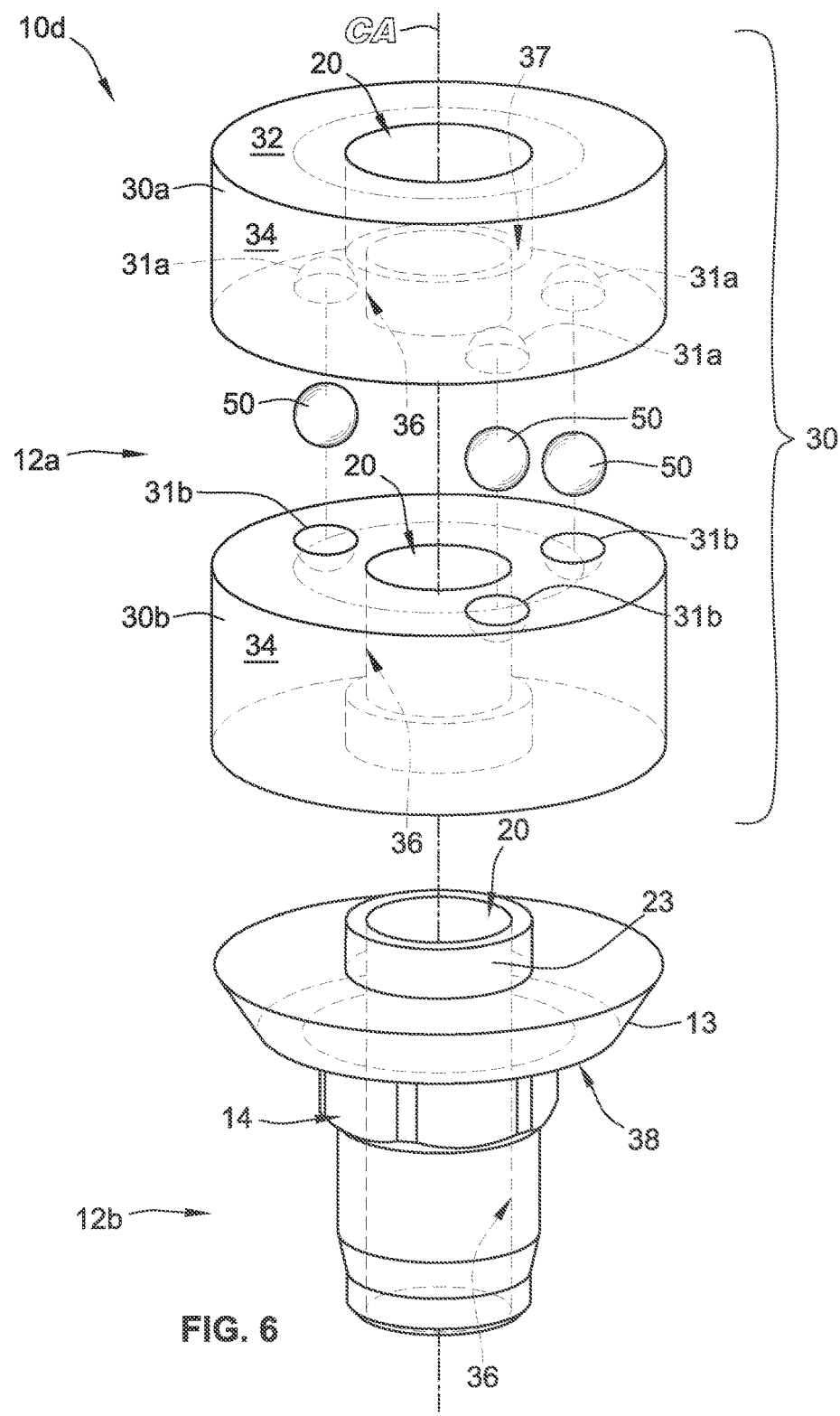
FIG. 6 is an exploded perspective view of an attachment member illustrating a method of positioning radiopaque information markers internal to a body of the attachment member during fabrication of the same according to some aspects of the present disclosure.

As best shown in FIGS. 1B and 1C, the attachment member 10a is a monolithic one-piece member in that the supragingival region 12a and the subgingival region 126 are formed from the same material (e.g., acrylic) except for the set of radiopaque information markers 50 therein which is formed from a material having a different opacity than the rest of the body 30 of the attachment member 10a. Alternatively, the supragingival region 12a and/or the subgingival region 12b are formed from one or more separate parts (e.g., as shown in FIGS. 6 and 7) that are permanently and/or securely attached (e.g., sonic welding, glued, press-fit, etc.) together to form a one-piece attachment member 10a. In such an alternative, the supragingival region 12a can be made of a first material (e.g., acrylic with a first opacity), the radiopaque information markers 50 can be made of second material (e.g., acrylic with a second opacity), and the subgingival region 12b can be made of a third material (e.g., metal, such as titanium).

Figure 2A:
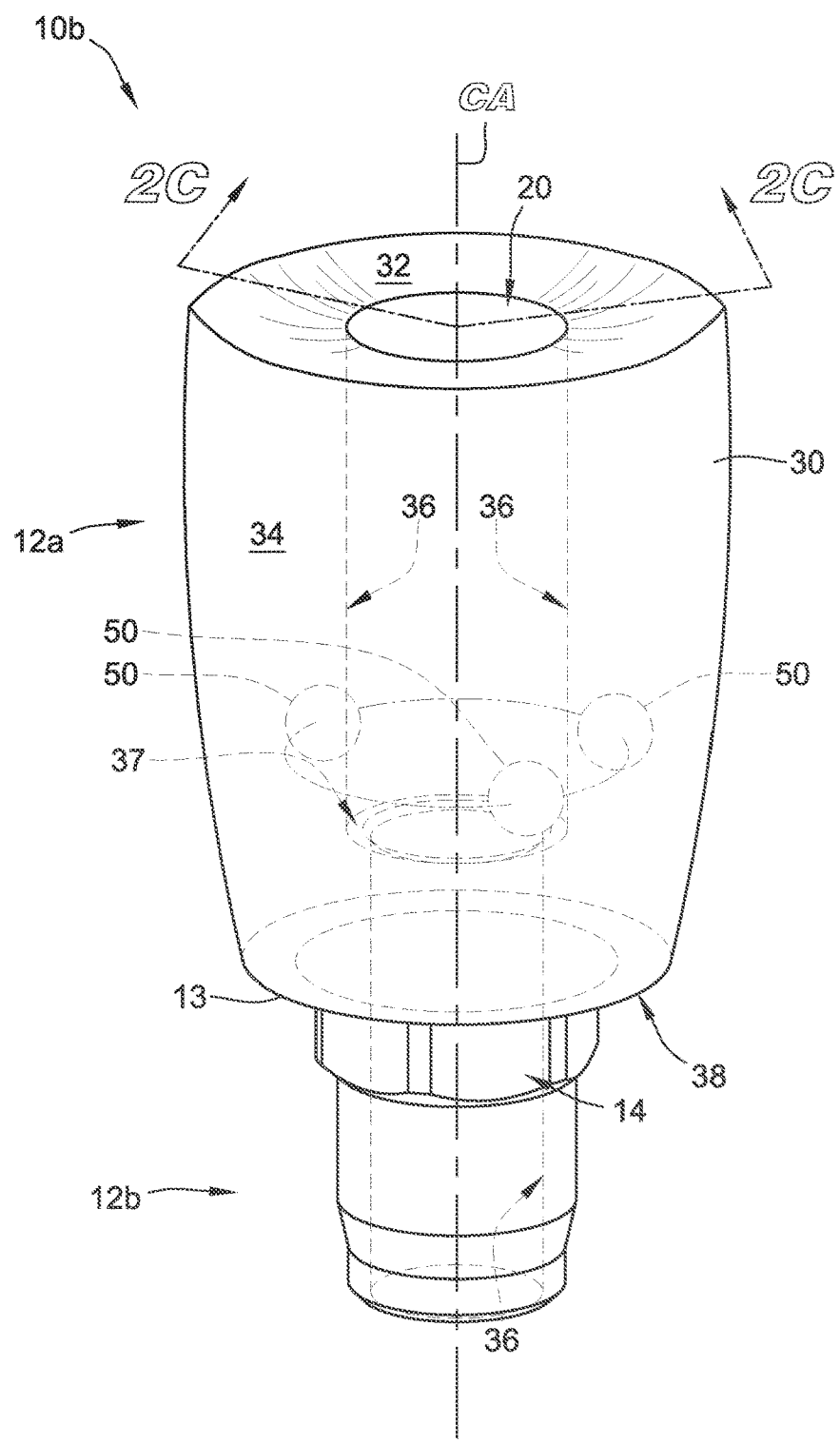
FIG. 2A is a perspective view of a generally anatomically shaped attachment member having internal radiopaque information markers according to some aspects of the present disclosure.
Figure 2B:
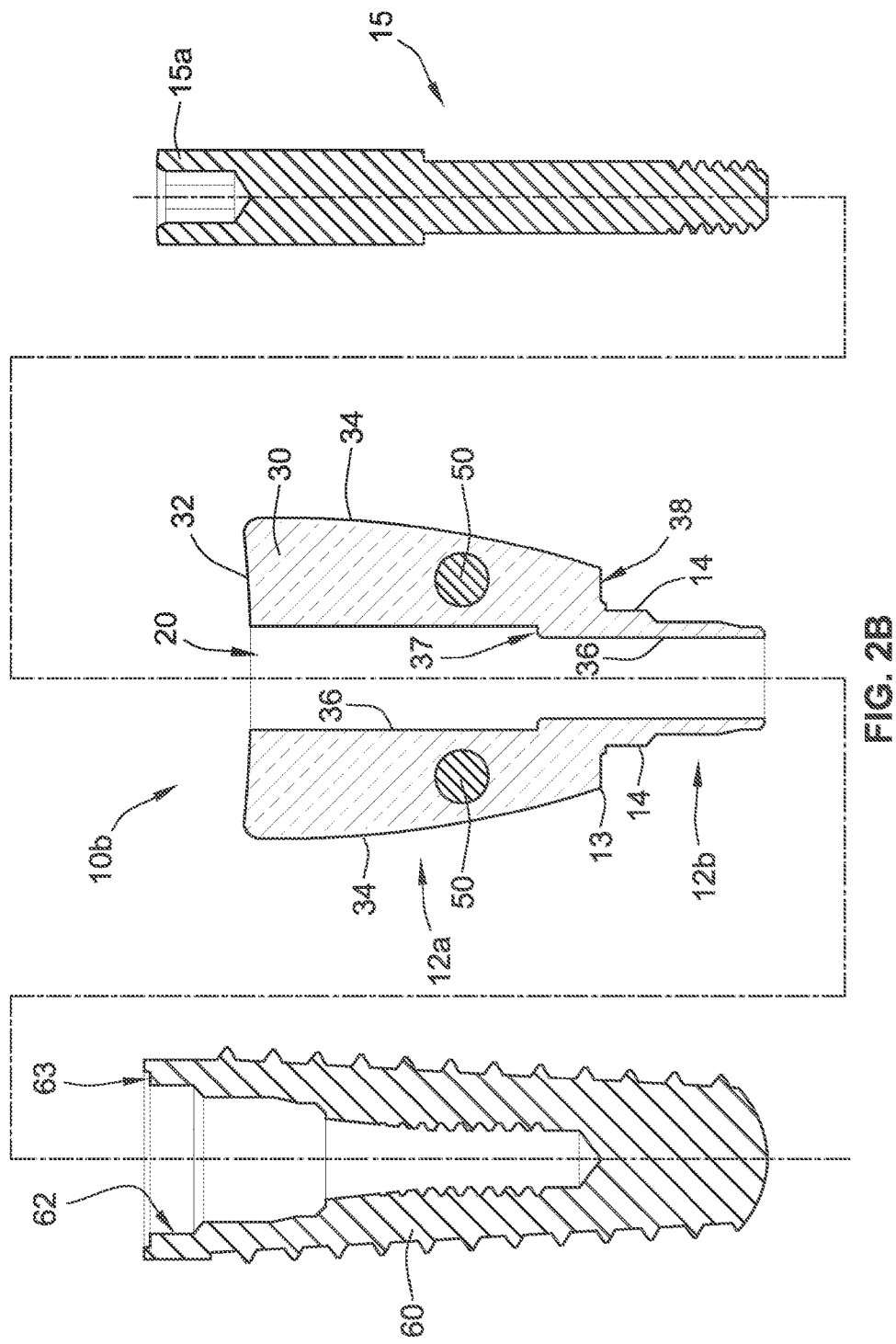
FIG. 2B is an exploded cross-sectional front view of the attachment member of FIG. 2A relative to a dental implant and a screw.
Figure 2C:
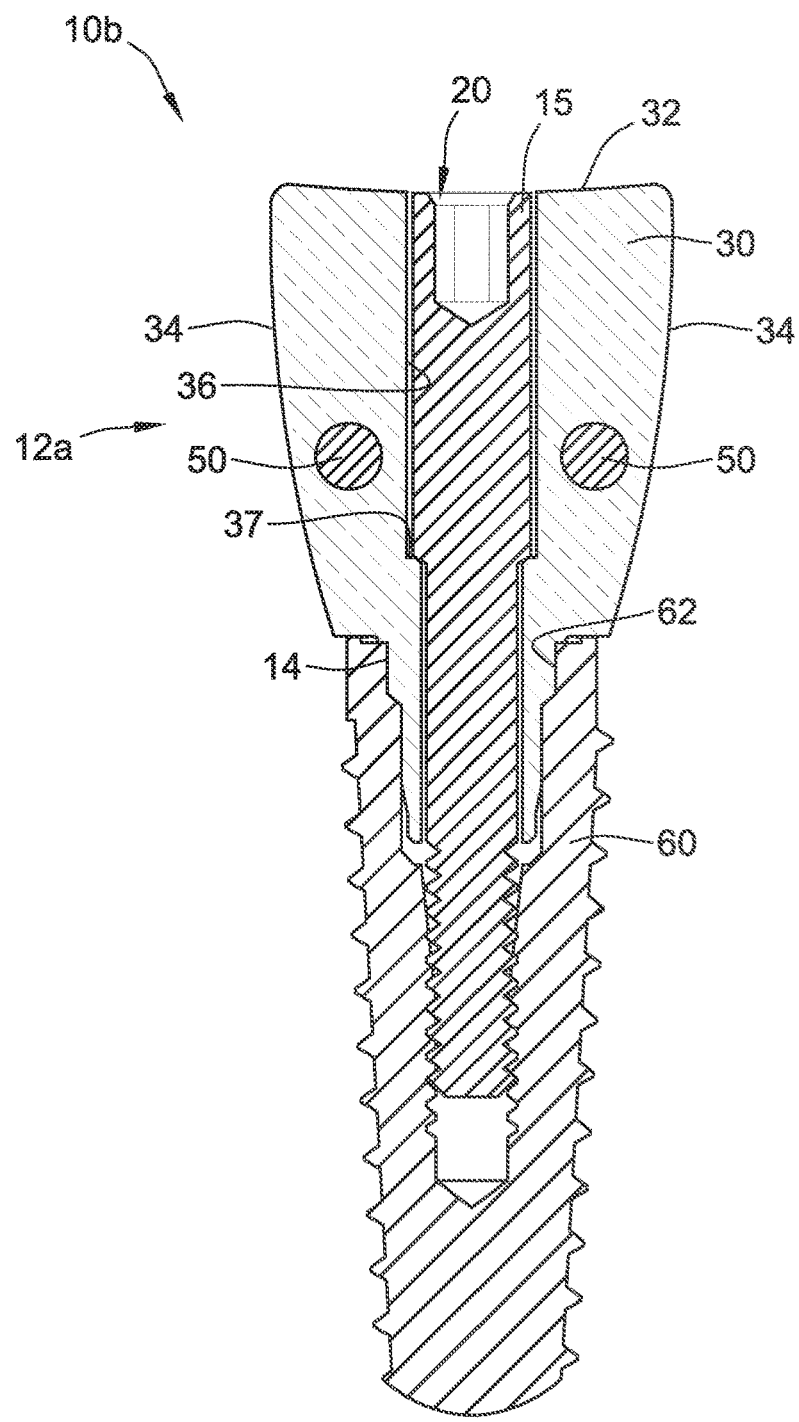
FIG. 2C is an assembled cross-sectional front view of the attachment member, the dental implant, and the screw of FIG. 2B.

Referring now to FIGS. 2A-2C, an attachment member 10b is illustrated that is similar to the attachment member 10a, except that an upper or supragingival region 12a of the attachment member 10b has a generally anatomic emergence-profile shape compared to the generally cylindrical shape of the upper or supragingival region 12a of the attachment member 10a. The other aspects of the attachment member 10b are illustrated with like reference numbers indicating like components/features as shown and described with reference to the attachment member 10a of FIGS. 1A-1C. Another difference between the attachment members 10a and 10b is that the transition section 13 (e.g., undercut) of the attachment member 10b is formed as part of the supragingival region 12a of the attachment member 10b.

Referring now to FIGS. 3A-3D, an attachment member 10c is illustrated that is similar to the attachment members 10a and 10b with like reference numbers indicating like components/features as shown and described with reference to the attachment members 10a and 10b. The attachment member 10c mainly differs from the attachment members 10a and 10b (FIGS. 1A-2C) in that the attachment member 10c (FIGS. 3A-3D) is formed by a cap portion 11a and an insert portion 11b. The cap portion 11a has a generally anatomical tooth shape (e.g., like the attachment member 10b), although the cap portion 11a can have any shape (e.g., cylindrical, square, oval, etc.).

The cap portion 11.a and the insert portion 11b are removably connectable, for example, by a snap-on connection and/or in a slide-on fashion) such that the screw 15 can attach the insert portion 11b to the dental implant 60 and the cap portion 11a can then be attached to the insert portion 11b thereafter. Such a configuration allows for easy removal of the cap portion 11a of the attachment member 10c. As such, a clinician can readily analyze and/or modify (e.g., remove and/or add material thereto) the cap portion 11.a to impact/alter gingiva healing therearound. Thus, the cap portion 11a can be a patient-specific component. With the set of radiopaque information markers 50 buried inside the cap portion 11a, modification of the cap portion 11a (e.g., especially the upper occlusal surface 32 of the cap portion 11a) does not impact the pre-defined relationship of the set of radiopaque information markers 50 and the non-rotational structures 14, 27, 29, and 62 and/or the seating/table surfaces 38 and 63. Thus, unlike some of the prior scan members, the upper occlusal surface 32 of the cap portion 11a of the attachment member 10c can be modified as desired to occlude with an opposing tooth in the mouth of a patient without destroying or modifying the radiopaque information markers 50 of the attachment member 10c. The described modification of the cap portion 11a can be manual by a clinician and/or automatic using a robot, a milling machine, a rapid prototype machine, any combination thereof, or the like.

The insert portion 11b has an upper or supragingival region 22a and a lower or subgingival region 22b, which are separated by a transition section 13. The subgingival region 22b includes a non-rotational structure 14 for mating with a corresponding non-rotational structure 62 of the dental implant 60. The supragingival region 22a of the insert portion 11b includes a retention groove or structure 26 and a non-rotational structure 27. The retention groove 26 is configured to mate in a snap-on axial holding engagement with corresponding male circumferential feature(s) or structure(s) 28 of cap portion 11a. Alternatively the cap portion 11a can include the retention groove 26 and the insert portion 11b can include the corresponding male circumferential feature(s) 28.

The non-rotational structure 27 of the insert portion 11b is configured to mate in a slidable engagement with a corresponding non-rotational structure 29 of the cap portion 11a to prevent relative rotation of the cap portion 11a and the insert portion 11b. In the illustrated implementation, the non-rotational structure 27 of the insert portion 11b generally extends from a top or upper surface of the insert portion 11b to the transition section 13. Details on and examples of anti-rotational structures for dental posts (e.g., supragingival regions of temporary abutments) are shown in U.S. Pat. Nos. 6,120,293, 6,159,010, and 8,002,547, each of which is commonly owned by the assignee of the present application and is hereby incorporated by reference herein in its entirety.

Figure 3B:
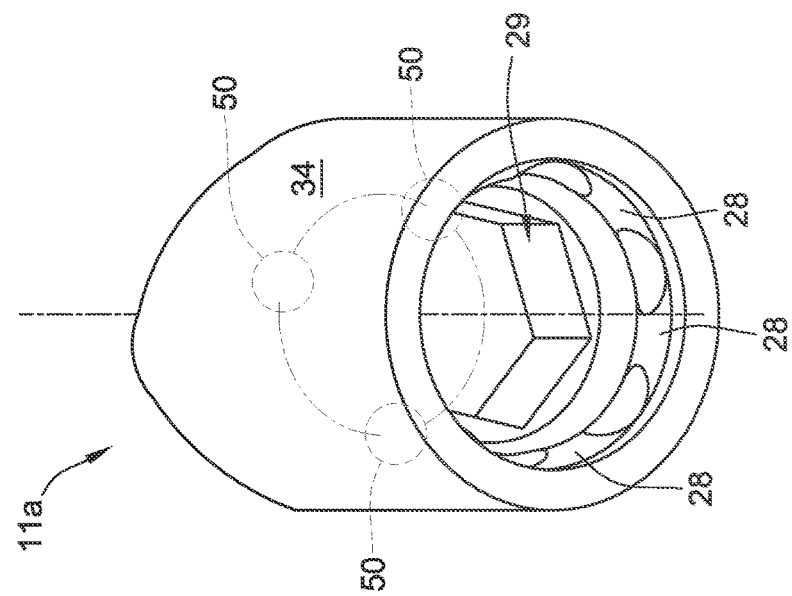
FIG. 3B is another perspective view of the generally anatomically shaped attachment member of FIG. 3A.
Figure 3A:
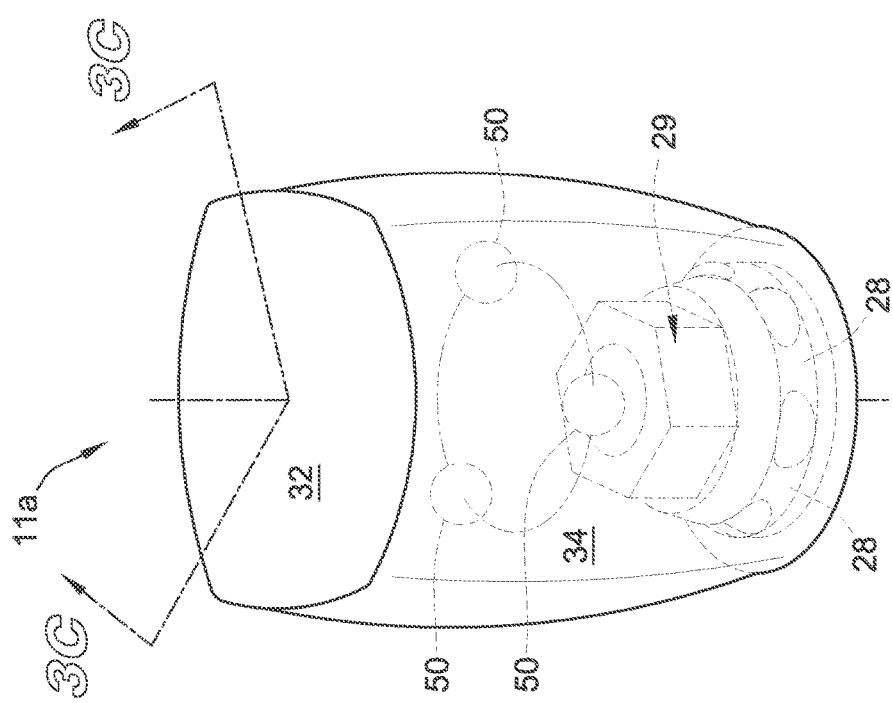
FIG. 3A is a perspective view of a generally anatomically shaped attachment member having internal radiopaque information markers according to some aspects of the present disclosure.
Figure 3C:
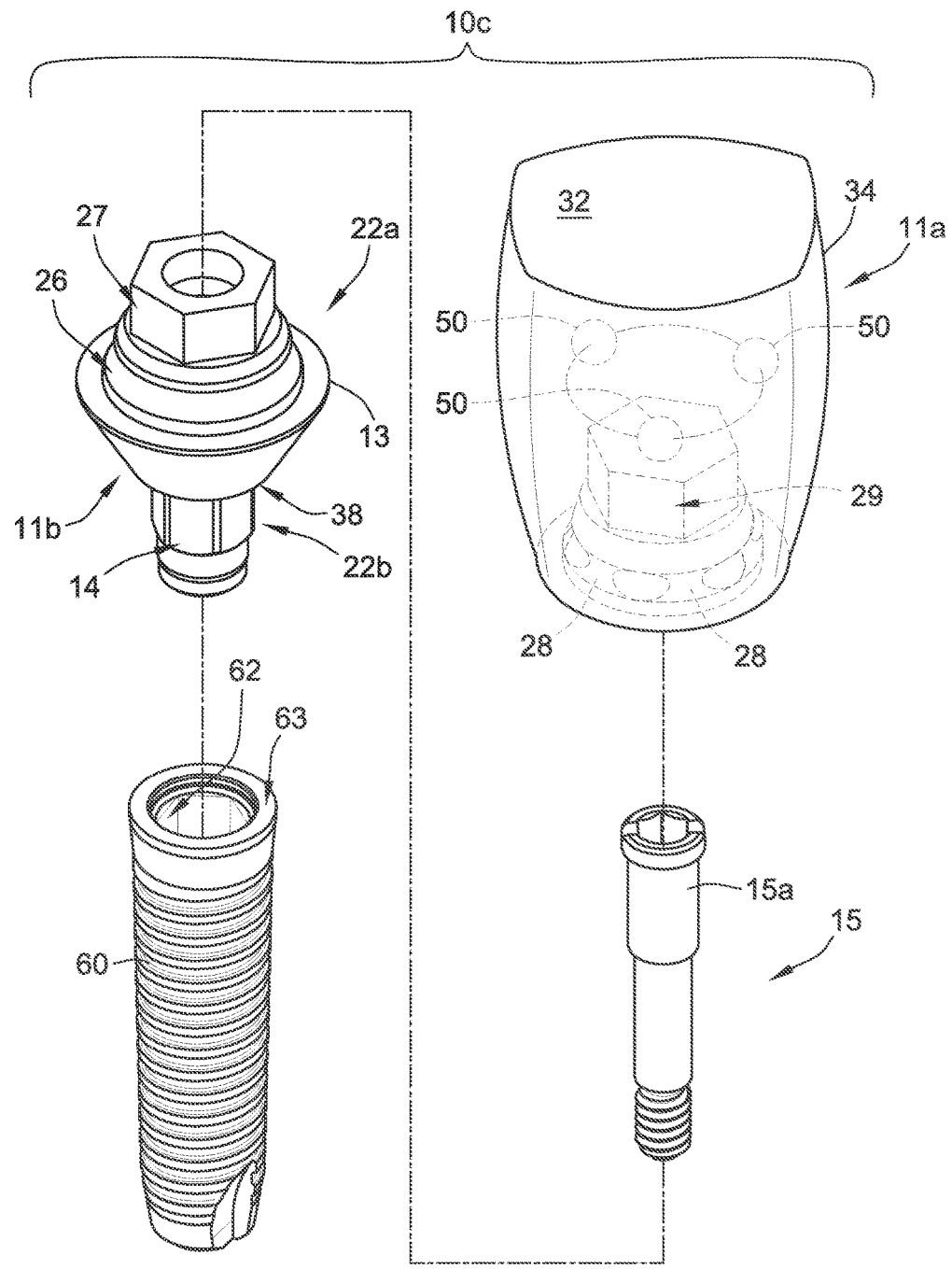
FIG. 3C is an exploded cross-sectional front view of the attachment member of FIGS. 3A and 3B relative to an insert, a dental implant and a screw.
Figure 3D:
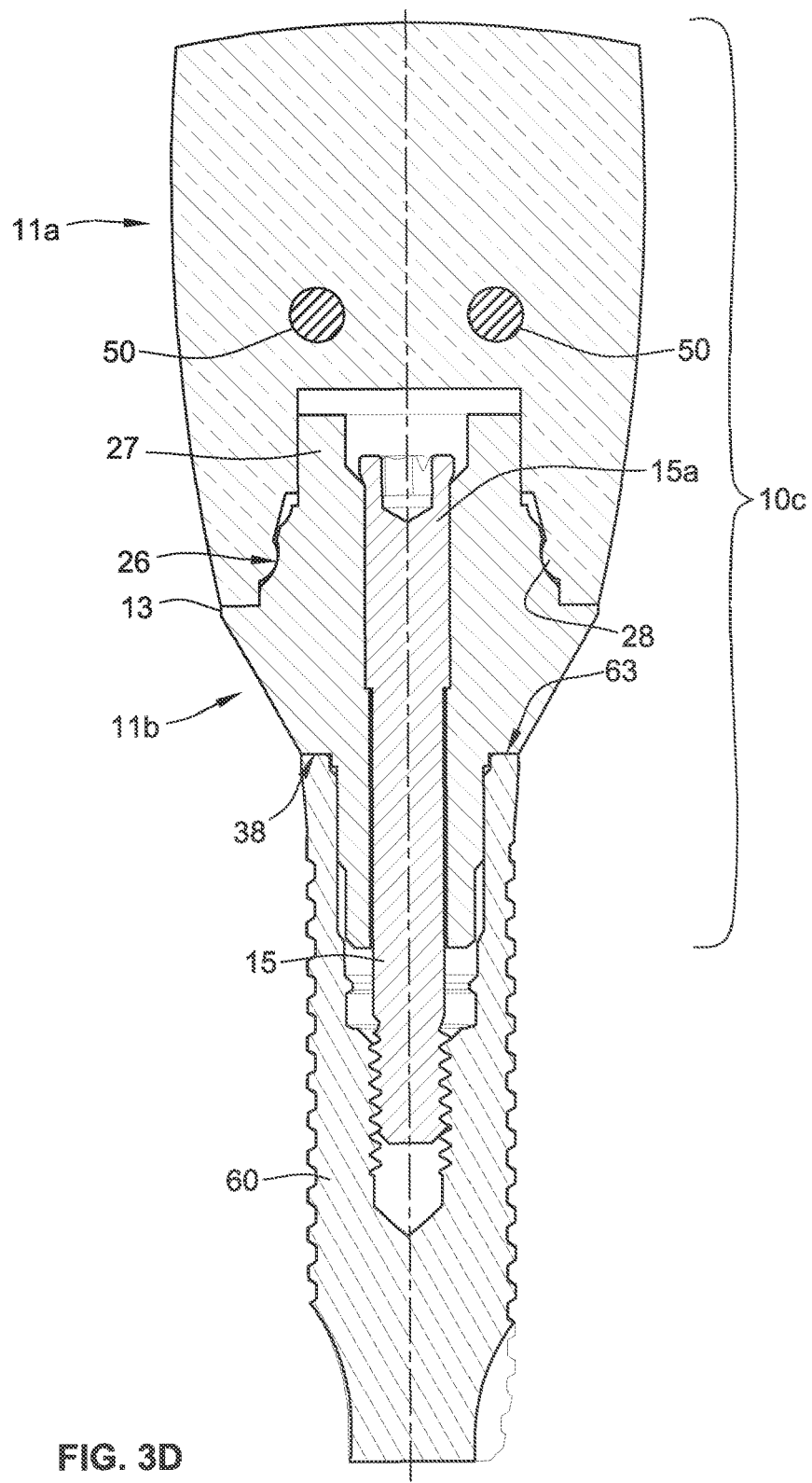
FIG. 3D is an assembled cross-sectional front view of the attachment member, the insert, the dental implant, and the screw of FIG. 3C.

As an alternative to the cap portion 11a snapping onto the insert portion 11b, the cap portion 11a can be fixed to the insert portion 11b using, for example, dental cement, glue, or other similar methods. The cap portion 11a may be fixed to the insert portion 11b by a clinician, unlike some prior scan members including caps, because the radiopaque information markers 50 in the body 30 of the attachment member 10c can be picked up or otherwise identified via a CT scan. Thus, unlike prior methods, it is not necessary to remove the cap portion 11a prior to scanning for information markers. Thus, the site in the patient's mouth including the attachment member 10c does not need to be disturbed by the removal of the cap portion 11a for identification of the radiopaque information markers 50. Further, use of the cap portion 11a after the insert portion 11b is coupled with the dental implant 60 (as shown in FIG. 3D) eliminates the requirement for the screw access bore 20 of the attachment member 10c to extend through the entire attachment member 10c and to the top occlusal surface 32, which typically requires a plug to be inserted during installation.

Referring to FIG. 4A, a clinician 51 is shown manually modifying and/or customizing one of the above-described attachment members 10a, 10b, including a set of radiopaque attachment markers 50 therein prior to installing the same in a mouth of a patient. That is, one way for the attachment members 10a, 10b; and 10c to be fabricated is by a clinician removing and/or adding material to a stock or standard attachment member to create one of the attachment members 10a, 10b, 10c, although in some implementations, the attachment members 10a, 10b, 10c are not modified and simply installed in the mouth of the patient as a stock/non-custom solution. The stock or standard attachment member can have an anatomical tooth shape (e.g., attachment members 10b, 10c) or a non-anatomical tooth shape (e.g., attachment member 10a). Such a manual method of modification can be accomplished chair side after the dental implant 60 is installed into the patient's mouth such that the patient can leave with an attachment member 10a, 10b, 10c acting as a temporary tooth and as a gingival healing abutment immediately after the dental implant 60 is installed.

In some implementations of the present concepts, a kit or package of attachment members can be supplied to the clinician. Each of the attachment members in the kit has a preformed anatomical tooth shape of a predetermined size and shape. The clinician can select the appropriate attachment member(s) and place the attachment member as-is or begin customization/modification as necessary for the particular patient. Thus, in such implementations, the clinician is supplied with a variety of preformed attachment members having different anatomical teeth shapes that can be modified/customized as necessary and attached to the dental implant 60.

When the clinician creates a custom attachment member by modifying an attachment member (e.g., attachment members 10a, 10b, 10c), the attachment member that is to be attached to the dental implant 60 is initially scanned using a CT scanner 54 (e.g., a cone beam CT scanner) (FIG. 4B) to obtain CT scan data of the attachment member. The CT scanning of the attachment member 10a, 10b, 10c generates the CT scan data associated with the attachment member 10a, 10b, 10c that can be used to create a virtual three-dimensional model of the attachment member 10a, 10b, 10c. Thus, the scanning of the attachment member 10a, 10b, 10c captures all of the external contours, sizes, and shapes of the attachment member 10a, 10b, 10c and further captures the contours, sizes, and shapes of the internal set of radiopaque information markers 50 in a digital format that can be virtually/digitally segmented (e.g., separating the radiopaque information markers 50 from the rest of the attachment member 10a, 10b, 10c) and/or displayed as a virtual three-dimensional model of the attachment member 10a, 10b, 10c on a display device (e.g., computer monitor).

Specifically, the entire attachment member 10a, 10b, 10c is CT scanned using CT scanner 54 (FIG. 4B) such that the virtual three-dimensional model of the attachment member 10a, 10b, 10c is a complete virtually-segmented replica of the attachment member 10a, 10b, 10c. By segmented, it is meant that the CT scan data is processed by a computer running software that virtually/digitally segments the CT scan data such that the set of radiopaque information markers 50 therein are virtually/digitally separate from the rest of the attachment member such that a virtually-segmented three-dimensional model of the attachment member 10a, 10b, 10c can be displayed. For example, the radiopaque information markers 50 are displayed in a first color (e.g., red) and the rest of the attachment member 10a, 10b, 10c is displayed in a second color (e.g., blue) different from the first color. Alternatively, the entire attachment member 10a, 10b, 10c is displayed with a single color (e.g., black, green, etc.), but the outer surfaces of the attachment member 10a, 10b, 10c are hidden and/or transparent such that the radiopaque information markers 50 are visible on the display.

Prior to CT scanning the attachment member 10a, 10b, 10c, the attachment member 10a, 10b, 10c can be positioned within and/or attach to a fixture 55 (FIG. 4B). The fixture 55 can be, for example, a base (e.g., a block of material) that includes a non-rotational feature (e.g., a hexagonal socket, etc.) with a central axis, where the non-rotational feature is configured to mate with the corresponding non-rotational structure 14 (e.g., a hexagonal boss, etc.) of the attachment member 10a, 10b, 10c. Thus, coupling of the attachment member 10a, 10b, 10c to the fixture 55 automatically orients the attachment member 10a, 10b, 10c (1) such that the non-rotational structure 14 of the attachment member 10a, 10b, 10c corresponds with the orientation of the non-rotational feature of the fixture 55; (2) such that the central axis CA of the attachment member 10a, 10b, 10c corresponds with (e.g., is coincident with) the central axis of the non-rotational feature of the fixture 55; and (3) such that the seating surface 38 of the attachment member 10a, 10b, 10c corresponds with a top surface 55a of the fixture 55. The fixture 55 (and its non-rotational feature) is positioned at a known location (e.g., position and orientation) with respect to the CT scanner 54 used to scan the attachment member 10a, 10b, 10c. Thus, attachment of the attachment member 10a, 10b, 10c to the fixture 55 automatically provides the CT scanner (and/or scanning software) with (1) the orientation of the non-rotational structure 14 of the attachment member 10a, 10b, 10c; (2) the location of the central axis CA of the attachment member 10a, 10b, 10c; (3) the location of the seating surface 38 of the attachment member 10a, 10b, 10c; and (4) the location of the screw access hole 20 of the attachment member 10a, 10b, 10c. As such, the accuracy of the CT scan (e.g., the acquisition of the CT scan data associated with the attachment member 10a, 10b, 10c) of the attachment member 10a, 10b, 10c can be improved by reducing the amount of CT scan data that needs to be stitched or merged together to develop the segmented-virtual three-dimensional model of the attachment member 10a, 10b, 10c. For example, knowledge of the orientation of the non-rotational structure 14 of the attachment member 10a, 10b, 10c permits the scanning software to automatically include interface geometry (e.g., the non-rotational structure 14) of the attachment member 10a, 10b, 10c (e.g., using stock data associated with known attachment member 10a, 10b, 10c interfaces that mate with the fixture 55). That is, the portion of the CT scan data associated with the non-rotational structure 14 of the attachment member 10a, 10b, 10c is not needed and can be replaced with stock known data that is stitched with the rest of the CT scan data. Similarly, for another example, knowledge of the central axis CA of the attachment member 10a, 10b, 10c permits the scanning software to automatically include a screw access hole of the attachment member 10a, 10b, 10c (e.g., a bore for receiving the screw therethrough to attach the attachment member 10a, 10b, 10c to the dental implant 60) in the same, or similar, manner described above in reference to the interface geometry.

Figure 5:
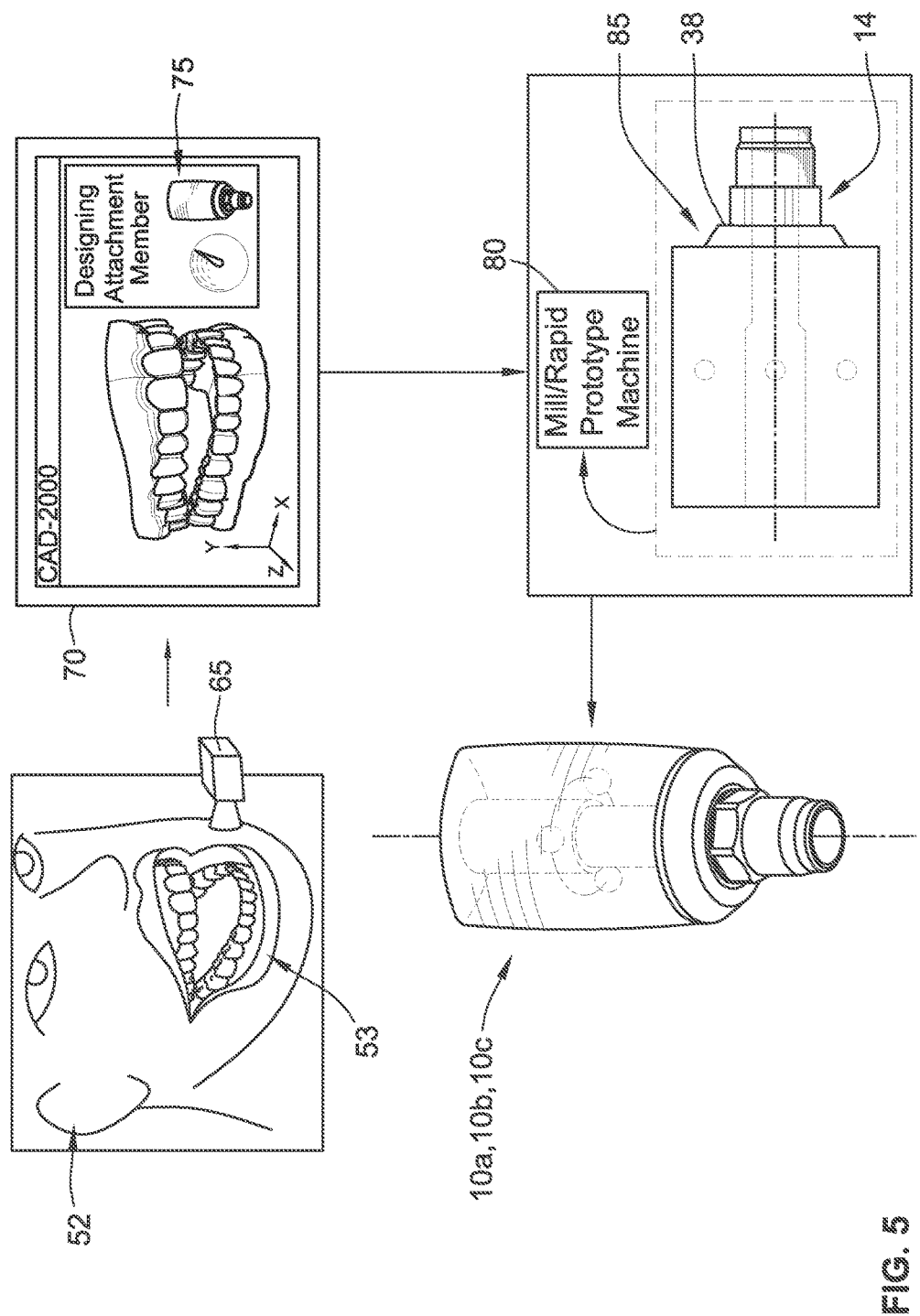
FIG. 5 is an animated flow chart illustrating a virtual design and fabrication of a generally anatomically shaped attachment member from a stock blank according to some aspects of the present disclosure.

FIG. 5 illustrates an alternative approach in which the attachment members 10a, 10b, 10c can be virtually/digitally designed and fabricated using a milling machine (e.g., a 5 axis milling machine) and/or a rapid prototype machine 80 prior to the dental implant 60 being installed into a mouth 53 of a patient 52, as opposed to the manual modification method described in reference to FIGS. 4A and 4B. As shown in FIG. 5, prior to any dental implants being installed, a CT scan (e.g., CBCT scan) and/or an intraoral scan (IOS) can be taken of the mouth 53 of the patient 52 using one or more scanners/cameras 65 (e.g., x-ray scanners, CT scanners, CBCT scanners, IOS scanner, etc.). Scan data (e.g., IOS scan data, CT scan data, etc.) and/or virtual three-dimensional models generated from the CT and/or IOS scans is transferred to a computer system 70 including software (e.g., CAD software, graphical imaging software, segmenting software, etc.) configured to process the generated scan data and/or virtual three-dimensional models and virtually design an attachment member for the patient 52. Specifically, the software evaluates the scan data and/or virtual three-dimensional models associated with the teeth and the gingival tissue of the patient 52 surrounding and adjacent to the planned implant site (e.g., site where a tooth will be removed and replaced with an implant) and accordingly designs a virtual attachment member 75. After the virtual attachment member 75 is designed, virtual attachment member data is generated. The virtual attachment member data includes instructions for the milling and/or rapid prototype machine 80 to execute in order to fabricate the attachment member (e.g., the attachment member 10a, 10b, 10c). Additional details on creating bone and soft-tissue digital dental models (e.g., virtual three-dimensional models) from the CT scan and the IOS scan can be found in U.S. Patent Application Publication No. 2011/0129792, which is hereby incorporated by reference herein in its entirety.

As shown in FIG. 5, in some implementations, the virtual attachment member 75 is milled from a blank attachment member 85 including a set of radiopaque information markers 50 therein, which are positioned in a predetermined/known relationship to a preformed non-rotational structure 14 of the blank attachment member 85 and to a preformed seating surface 38 of the blank attachment member 85. Depending on the virtual attachment member data, an operator of the milling machine and/or a rapid prototype machine 80 can be instructed to place one of a multitude of differently sized blank attachment members 85 therein for fabrication (e.g., milling/rapid prototyping). Once the fabrication is complete, the finalized attachment member 10a, 10b, 10c can be removed from the milling machine and/or a rapid prototype machine 80 and attached to a dental implant installed in the mouth 53 of the patient 52. Unlike the implementation described in connection with FIGS. 4A and 4B, there is no need to couple the finalized attachment member 10a, 10b, 10c (FIG. 5) to the fixture 55 for CT scanning, because all of contours of the attachment member and the location of the set of radiopaque information markers 50 therein are already known from the designing process carried out using the computer 70.

As an alternative to the blank attachment member 85 having a preformed non-rotational structure 14 and a preformed seating surface 38, the blank attachment member 85 can simply be a block of material with the radiopaque information markers 50 therein at a known location relative to one or more outer surfaces of the blank attachment member 85. In such implementations, the fabrication process would include the milling of the blank attachment member 85 to include the non-rotational structure 14 and the preformed seating surface 38 in addition to the other contours of the finalized attachment member 10a, 10b, 10c (FIG. 5).

Referring now to FIG. 6, a pre-assembly exploded view of an attachment member 10d is shown. The attachment member 10d is the same as, or similar to the attachment members 10a, 10b, 10c, where like reference numbers indicate like components/features as shown and described with reference to the attachment members 10a, 10b, 10c. FIG. 6 illustrates an exemplary manner of making/fabricating the attachment members of the present disclosure with the radiopaque information markers 50 internal to the body 30. As shown, prior to the attachment member 10d being assembled and taking its final form (e.g., as shown in FIGS. 1A-1C) as a unitary component, the attachment member 10d includes a body 30 with a first body portion 30a and a second body portion 30b, a lower or subgingival portion 12b, and a set of radiopaque information markers 50. The first body portion 30a includes cavities 31a and the second body portion 30b includes cavities 31b that cooperate to receive and contain therein the set of radiopaque information markers 50. The cavities 31a, 31b are sized and shaped to receive and contain therein the radiopaque information markers 50 in a manner such that the radiopaque information markers 50 do not move (e.g., rotate, translate, bounce, or otherwise) within the cavities 31a, 31b once the first and second body portions 30a, 30b are attached together, for example, by sonic welding, glue, press-fit (not shown), any combination thereof, or otherwise.

The lower or subgingival portion 12b of the attachment member 10d includes an annular protrusion 23 that extends upward from a top surface of the transition section 13. The annular protrusion 23 is sized and shaped to be press fit into the lower end of the second body portion 30b such that the body 30 is attached or fixed to the lower or subgingival portion 12b in a non-removable fashion (e.g., in a manner such that the body is not readily removable from the annular protrusion 23). Alternatively to the annular protrusion 23 being annular (e.g., circular/cylindrical), the annular protrusion 23 can have any other shape and size, such as, for example, square, oval, rectangle, triangle, hexagonal, etc. In some other alternative implementations, the lower or subgingival portion 12b does not include an annular protrusion 23 and the second body portion 30b is attached directly to the top surface of the transition section 13 by, for example, glue, sonic welding, a combination thereof, or the like.

While the attachment member 10d is shown as having two body portions 30a and 30b and the lower or subgingival portion 12b being separate and distinct components in the preassembled state (FIG. 6), various other implementations are contemplated. For example, the lower or subgingival portion 12b can be monolithic with the second body portion 30b where the first body portion 30a is the only separate and distinct non-monolithic part of the attachment member 10d pre-assembly (not shown). Further, the body 30 can be divided up into more than two portions (e.g., three body portions, four body portions, five body portions, etc.), such as, for example, when the radiopaque information markers 50 are positioned in different planes relative to horizontal. For example, in implementations where some of the radiopaque information markers 50 are in a first plane and the rest are in a second plane parallel thereto but offset relative to vertical, the pre-assembly body 30 may be in three portions (not shown).

Further, while the first and second body portions 30a, 30b are both shown as including cavities 31a, 31b that cooperate to contain the radiopaque information markers 50 therein, it is contemplated that in some implementations, only one of the first and second body portions 30a, 30b includes a cavity therein for containing the radiopaque information markers 50. In such implementations, the radiopaque information markers 50 may, for example, be cube-shaped (see FIG. 8C) where the cavities have a corresponding cube-shape to fully receive the cube-shaped radiopaque information markers 50c (FIG. 8C) therein and the other body portion merely abuts the exposed surface of the cube-shaped radiopaque information markers 50c in the cavities. Various other shapes and sizes of the radiopaque information markers 50 and corresponding cavities 31 are contemplated as shown in FIGS. 8A-8G, described further herein.

Referring now to FIG. 7, a pre-assembly exploded view of an attachment member 10e is shown. The attachment member 10e is the same as, or similar to the attachment members 10a, 10b, 10c, where like reference numbers indicate like components/features as shown and described with reference to the attachment members 10a, 10b, 10c. FIG. 7 illustrates an exemplary manner of making/fabricating the attachment members of the present disclosure with the radiopaque information markers 50 internal to the body 30. As shown, prior to the attachment member 10e being assembled and taking its final form (e.g., as shown in FIGS. 1A-1C) as a unitary component, the attachment member 10e includes a body 30 with a first body portion 30a and a second body portion 30b, a lower or subgingival portion 12b, and a set of radiopaque information markers 50.

The attachment member 10e mainly differs from the attachment member 10d in that the attachment member 10e is assembled with telescoping body portions 30a, 30b, as compared with the abutting body portions 30a, 30b of the attachment member 10d. Assembly of the attachment member 10e includes coupling the second body portion 30b to the lower or subgingival portion 12b, positioning the radiopaque information markers 50 in the cavities 31 of the second body portion 30b, and then in a telescopic manner, sliding the first body portion 30a over the second body portion 30b, thereby securing the radiopaque information markers 50 in the cavities 31. As shown in FIG. 7, the radiopaque information markers 50 have a general rectangular shape and the cavities 31 have a corresponding shape to receive and contain the radiopaque information markers 50 therein in the same, or similar, fashion as described herein for the attachment member 10d.

A further difference between the attachment members 10d and 10e is that the lower or subgingival portion 12b of the attachment member 10e includes a non-rotational structure 23 instead of the annular protrusion 23 of the attachment member 10d. The non-rotational structure 23 of the attachment member 10e mates with a corresponding non-rotational feature 24 of the second body portion 30b as shown in FIG. 7. Alternatively, the attachment member 10e does not include the non-rotational structure 23 and the first and second body portions 30a, 30b are attached directly to the top surface of the transition section 13 by, for example, glue, sonic welding, a combination thereof, or the like.

In some implementations, in lieu of, or in addition to the radiopaque information markers 50 shown and described herein, radiopaque paint or ink can be applied on any portion of the attachment members of the present disclosure to be picked up in a CT scan and segmented therefrom. The radiopaque paint can be applied as any alphanumeric symbol or character 50a (FIG. 7) such that the applied symbols and/or characters 50a indicate information. For example, radiopaque paint can be applied to the outer surface of the second body portion 30b to spell out a manufacturer name (e.g., BIOMET 3i), a diameter of the attachment member 10e, a height of the attachment member 10e, any other information, etc., or any combination thereof. By covering the second body portion 30b with the first body portion 30a in the telescopic manner, any radiopaque paint applied to the exterior surface of the second body portion 30b is protected and maintained thereon to be picked up in a later CT scan of the attachment member 10e (e.g., when installed on a dental implant 60 in a mouth of a patient).

Various other methods of making the attachment members of the present disclosure are contemplated. For example, instead of positioning the radiopaque information markers 50 in cavities 31 as described in reference to FIGS. 6 and 7, the radiopaque information markers 50 can be formed in the body 30 using one or more lasers that cause a portion of material inside a monolithic body to alter (e.g., change structure) such that the altered portion of the body (e.g., the in situ formed radiopaque information markers) has a different opacity than the rest of the body, thereby forming a radiopaque information marker(s).

Referring generally to FIGS. 8A-8G, various alternative sets of radiopaque information markers are shown. Any one of the sets of radiopaque information markers in FIGS. 8A-8G can be used with any of the attachment members 10a-10e of the present disclosure. The sets of radiopaque information markers shown in FIGS. 8A-8G are exemplary and not exhaustive.

Figure 8A:
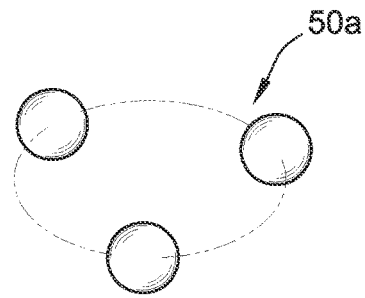
FIGS. 8A-8G are perspective views of various sets of radiopaque information markers for inclusion in a body of an attachment member according to some aspects of the present disclosure.
Figure 8B:
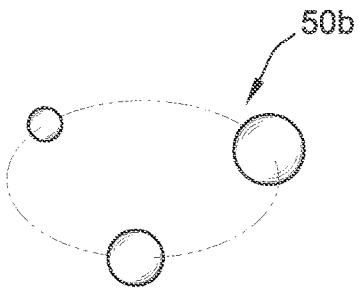
Figure 8C:
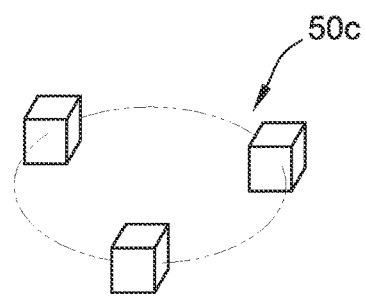
Figure 8D:
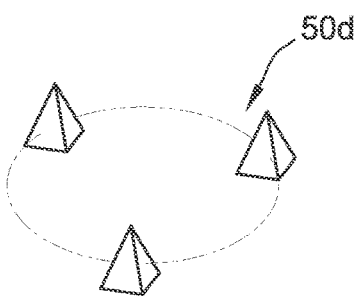
Figure 8E:
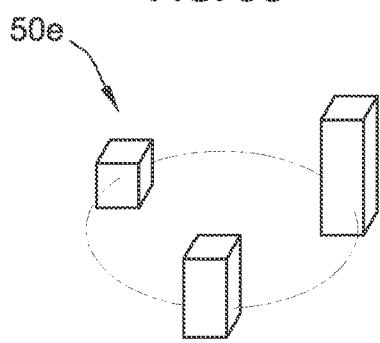
Figure 8F:
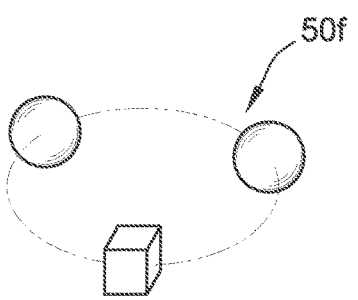
Figure 8G:
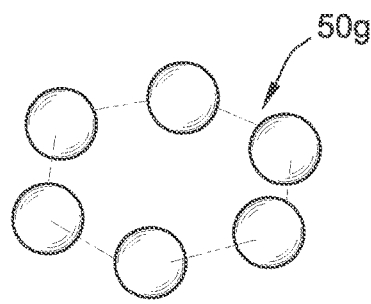

As shown in FIG. 8A, a first set of radiopaque information markers 50a is shown. The first set 50a includes three spheres, all of the same size, and all positioned with a center thereof in the same plane with respect to horizontal. As shown in FIG. 8B, a second set of radiopaque information markers 50b is shown. The second set 50b includes three spheres, all having a different size (e.g., diameter), and all positioned with a center thereof in the same plane with respect to horizontal. As shown in FIG. 8C, a third set of radiopaque information markers 50c is shown. The third set 50c includes three cubes, all of the same size, and all positioned with a center thereof in the same plane with respect to horizontal. As shown in FIG. 8D, a fourth set of radiopaque information markers 50d is shown. The fourth set 50d includes three pyramids, all of the same size, and all positioned with a center thereof in the same plane with respect to horizontal. As shown in FIG. 8E, a fifth set of radiopaque information markers 50e is shown. The fifth set 50e includes three rectangular cuboids, all having a different size (e.g., a different height), and all positioned with a bottom surface thereof in the same plane). As shown in FIG. 8F, a sixth set of radiopaque information markers 50f is shown. The sixth set 50f includes two spheres and one cube, the spheres having the same size, and all of the radiopaque information markers 50f being positioned with a center thereof in the same plane with respect to horizontal (e.g., a center of each of the two spheres and a center of the cube being in the same plane). As shown in FIG. 8G, a seventh set of radiopaque information markers 50g is shown. The seventh set 50g includes six spheres, all having the same size, and all positioned with a center thereof in the same plane with respect to horizontal. Various other shapes, sizes, and configurations for the radiopaque information markers of the present disclosure are contemplated.

Figure 9:
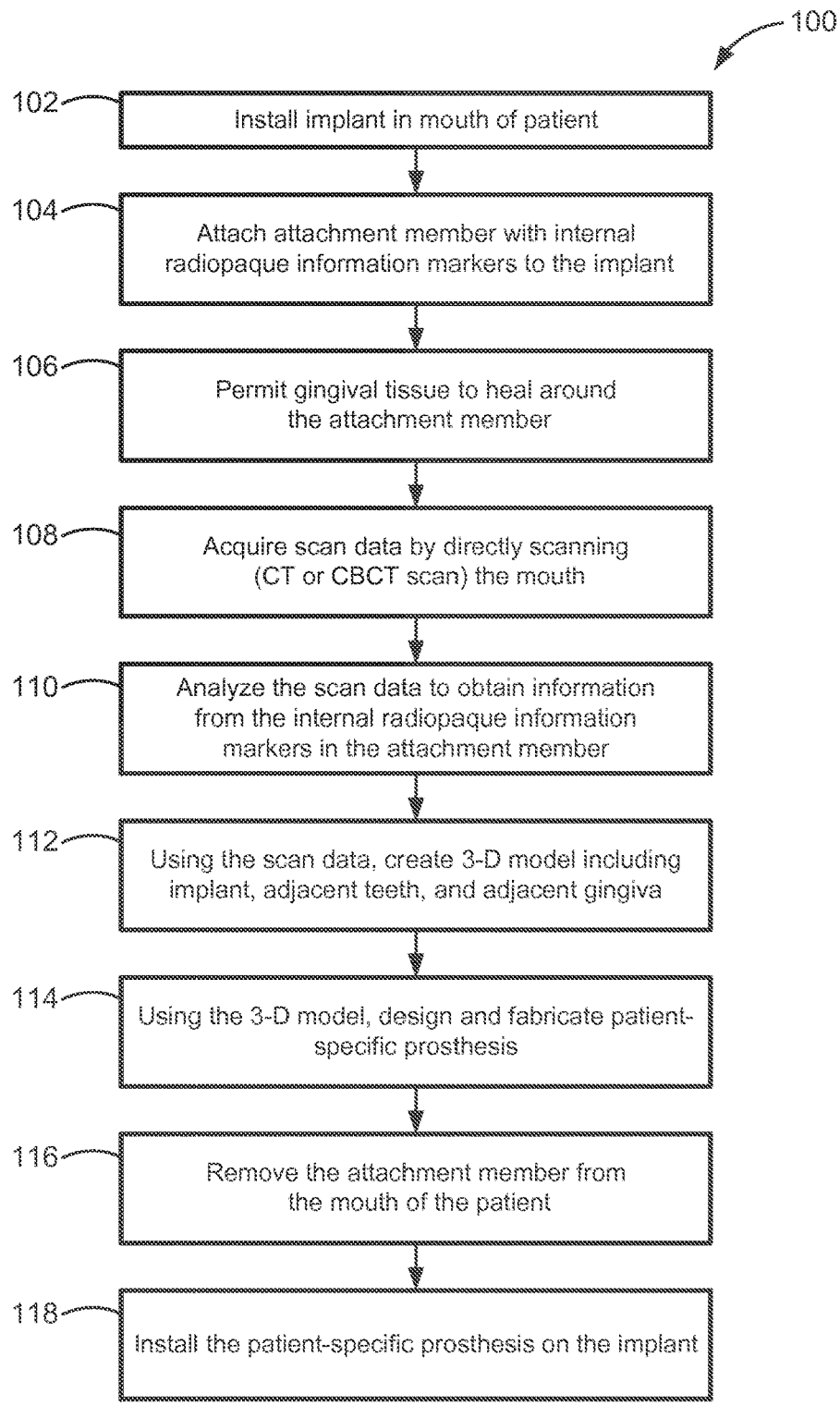
FIG. 9 is a flow chart of a method for manufacturing a permanent tooth prosthesis according to some aspects of the present disclosure.

Now referring to FIG. 9, a method 100 of manufacturing a patient-specific prosthesis (e.g., a final prosthesis) for attachment to a dental implant 60 installed in a mouth of a patient is described in reference to a flow chart. Initially, a dental implant (e.g., dental implant 60) is installed into the mouth of a patient (102). An attachment member (e.g., attachment member 10a, 10b, 10c) with internal radiopaque information markers 50 is attached to the dental implant 60 (104). In some implementations, the attachment member 10a, 10b, 10c is attached to the dental implant 60 in a non-rotational fashion (e.g., using complementary non-rotational structures 14, 62) and held in place using a screw fastener (e.g., screw 15). After the attachment member 10a, 10b, 10c is attached to the dental implant 60 (104), the patient's gingival tissue is permitted to heal around the attachment member 10a, 10b, 10c (106). The gingival tissue generally heals in a shape with an emergence contour profile that corresponds to the external contours (e.g., exterior side surface 34) of the attachment member 10a, 10b, 10c abutting the gingival tissue.

After the gingival tissue is permitted to heal (106) for a predetermined amount of time (e.g., a day, two weeks, a month, three months, six months, a year, etc.), the mouth of the patient is scanned with a CT scanner (e.g., CBCT scanner) to obtain/acquire CT scan data (108) of at least a portion of the mouth of the patient including the attachment member 10a, 10b, 10c therein, adjacent teeth, adjacent gingival tissue, etc. That is, the CT scan occurs without having to remove the attachment member 10a, 10b, 10c from the patient's mouth. Then the CT scan data is analyzed to obtain information from the internal radiopaque information markers 50 (110). The analyzing of the CT scan data can include processing the CT scan data using one or more computers executing one or more software programs, one of which being capable of virtually/digitally segmenting the various components/structures in the mouth of the patient. For example, one or more of the following structures can be identified and virtually/digitally segmented: (i) the exterior side surface 34 of the body 30 of the attachment member 10a, 10b, 10c1 (ii) the radiopaque information markers 50; (iii) the gingival tissue, including the gingival margin; (iv) the adjacent teeth and/or occluding teeth; (v) the jawbone, etc., or any combination thereof. According to some implementations, these structures are able to be identified and virtually/digitally segmented because each of these structures has a different opacity to radio waves used in CT scans (e.g., CBCT scans). In some implementations, to identify and virtually/digitally segment the gingival tissue, prior to the CT scan, a radiopaque wash is applied to the gingival tissue. Similarly, a radiopaque wash (the same or different than the radiopaque wash applied to the gingival tissue) can be applied to any other structure within the mouth of the patient. Typically, radiopaque washes are applied to soft tissues that do not pick-up/scan well or at all using some CT scanners.

Further, the analyzing (10) can include using the segmented structures to derive additional information, such as, for example, information associated with the attachment member 10a, 10b, 10c itself and/or information associated with the dental implant 60 and/or information associated with the gingival tissue. Then, the CT scan data is used to create and/or display (e.g., on a computer monitor display) a three-dimensional model of at least a portion of the patient's mouth (112) including, for example, a virtual three-dimensional model of a dental implant, a virtual three-dimensional model of adjacent teeth, and a virtual three-dimensional model of adjacent gingival tissue (e.g., having an anatomical shape and a gingival margin), where these structures are positioned in a manner corresponding to the real (i.e., non-virtual) structures in the patients mouth.

Then, using the three-dimensional model of the at least a portion of the patients mouth, a patient-specific prosthesis is designed and then fabricated (114). The patient-specific prosthesis can be one or two or more parts that couple to the dental implant installed in the patient's mouth to form a permanent/final tooth prosthesis. For example, the patient-specific prosthesis can include a patient-specific abutment and a patient-specific crown. With the patient-specific prosthesis fabricated (114), the attachment member 10a, 10b, 10c is removed from the mouth of the patient (116) and the patient-specific prosthesis (e.g., patient-specific abutment and patient-specific crown) is attached to the dental implant 60 (118).

Figure 10:
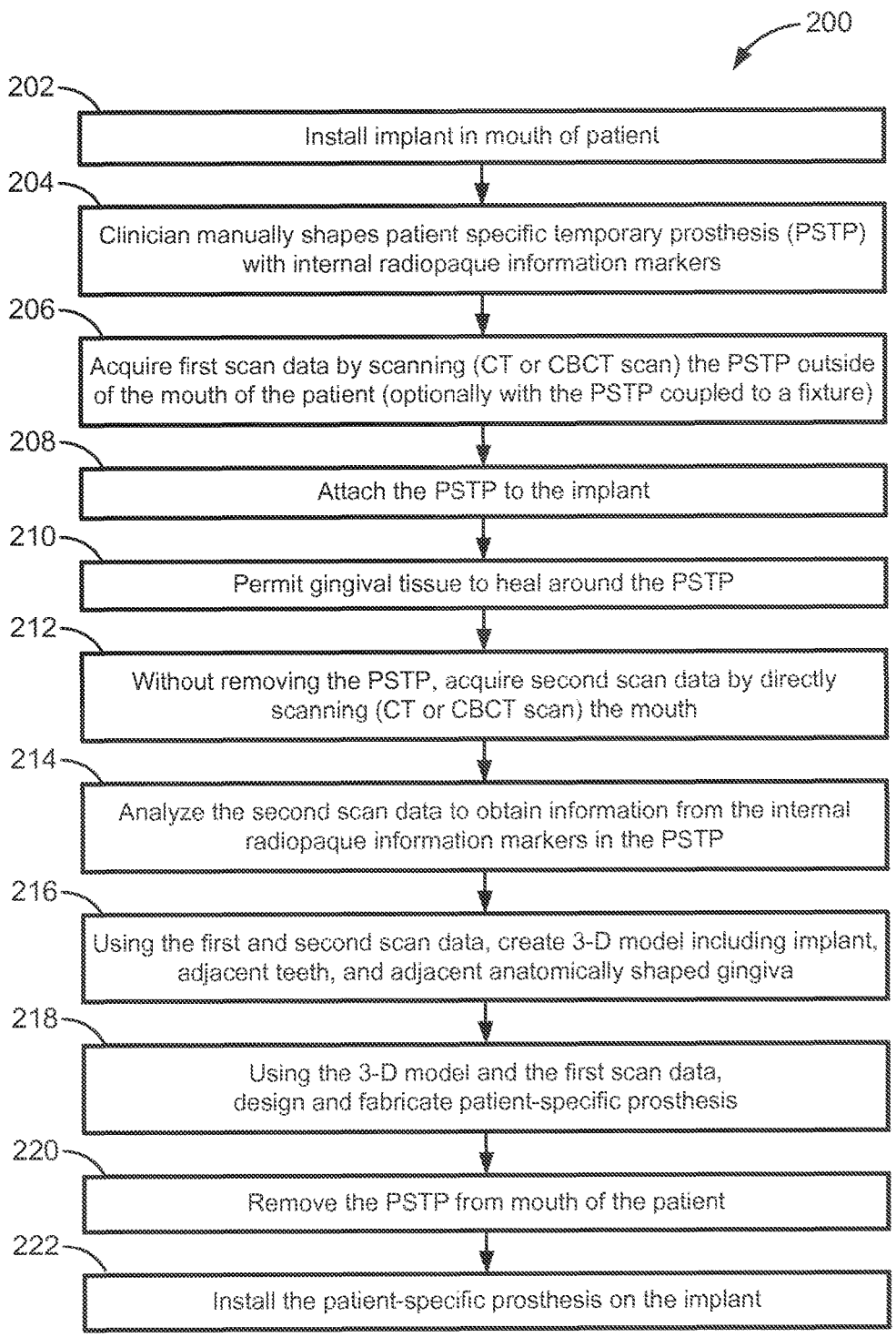
FIG. 10 is a flow chart of a method for manufacturing a permanent tooth prosthesis according to some aspects of the present disclosure.

Now referring to FIG. 10, a method 200 of manufacturing a permanent patient-specific prosthesis (e.g., a final prosthesis) for attachment to a dental implant 60 installed in a mouth of a patient is described in reference to a flow chart. Initially, a dental implant (e.g., dental implant 60) is installed into the mouth of a patient (202). Then an attachment member (e.g., attachment member 10a, 10b, 10c) with internal radiopaque information markers 50, such as, a PSTP-type attachment member, is manually shaped by a clinician (204). Then, the manually shaped/customized PSTP is scanned with a CT scanner (e.g., a CBCT scanner) outside the mouth of the patient to acquire first CT scan data (206). Optionally, the PSTP is coupled to a fixture 55 for the CT scanning. After being CT scanned, the PSTP with the internal radiopaque information markers 50 is attached to the dental implant 60 (208). In some implementations, the PSTP is attached to the dental implant 60 in a non-rotational fashion (e.g., using complementary non-rotational structures 14, 62) and held in place using a screw fastener e.g., screw 15). After the PSTP is attached to the dental implant 60 (208), the patient's gingival tissue is permitted to heal around the PSTP (210). The gingival tissue generally heals in a shape with an emergence contour profile that corresponds to the external contours (e.g., exterior side surface 34) of the PSTP abutting the gingival tissue.

After the gingival tissue is permitted to heal (210) for a predetermined amount of time (e.g., a day, two weeks, a month, three months, six months, a year, etc.), without removing the PSTP, the mouth of the patient is scanned with a CT scanner (e.g., CBCT scanner) to obtain/acquire second CT scan data (212) of at least a portion of the mouth of the patient including the PSTP therein, adjacent teeth, adjacent gingival tissue, etc. That is, the CT scan occurs without having to remove the PSTP from the patient's mouth. Then the second CT scan data is analyzed to obtain information from the internal radiopaque information markers 50 (214) in the same or similar fashion as described above in connection with element (110) in FIG. 9.

Then, the first and/or second CT scan data is used to create and/or display (e.g., on a computer monitor display) a three-dimensional model of at least a portion of the patient's mouth (216) including, for example, a virtual three-dimensional model of a dental implant, a virtual three-dimensional model of adjacent teeth, and a virtual three-dimensional model of adjacent gingival tissue (e.g., having an anatomical shape and a gingival margin), where these structures are positioned in a manner corresponding to the real (i.e., non-virtual) structures in the patient's mouth. In some implementations, only the second CT scan data is used to create the three-dimensional model of the at least a portion of the patient's mouth.

Then, using the three-dimensional model of the at least a portion of the patient's mouth and using the first CT scan data, a patient-specific prosthesis is designed and then fabricated (218). With the patient-specific prosthesis fabricated (218), the PSTP is removed from the mouth of the patient (220) and the patient-specific prosthesis (e.g., patient-specific abutment and patient-specific crown) is attached to the dental implant 60 (222).

Figure 11:
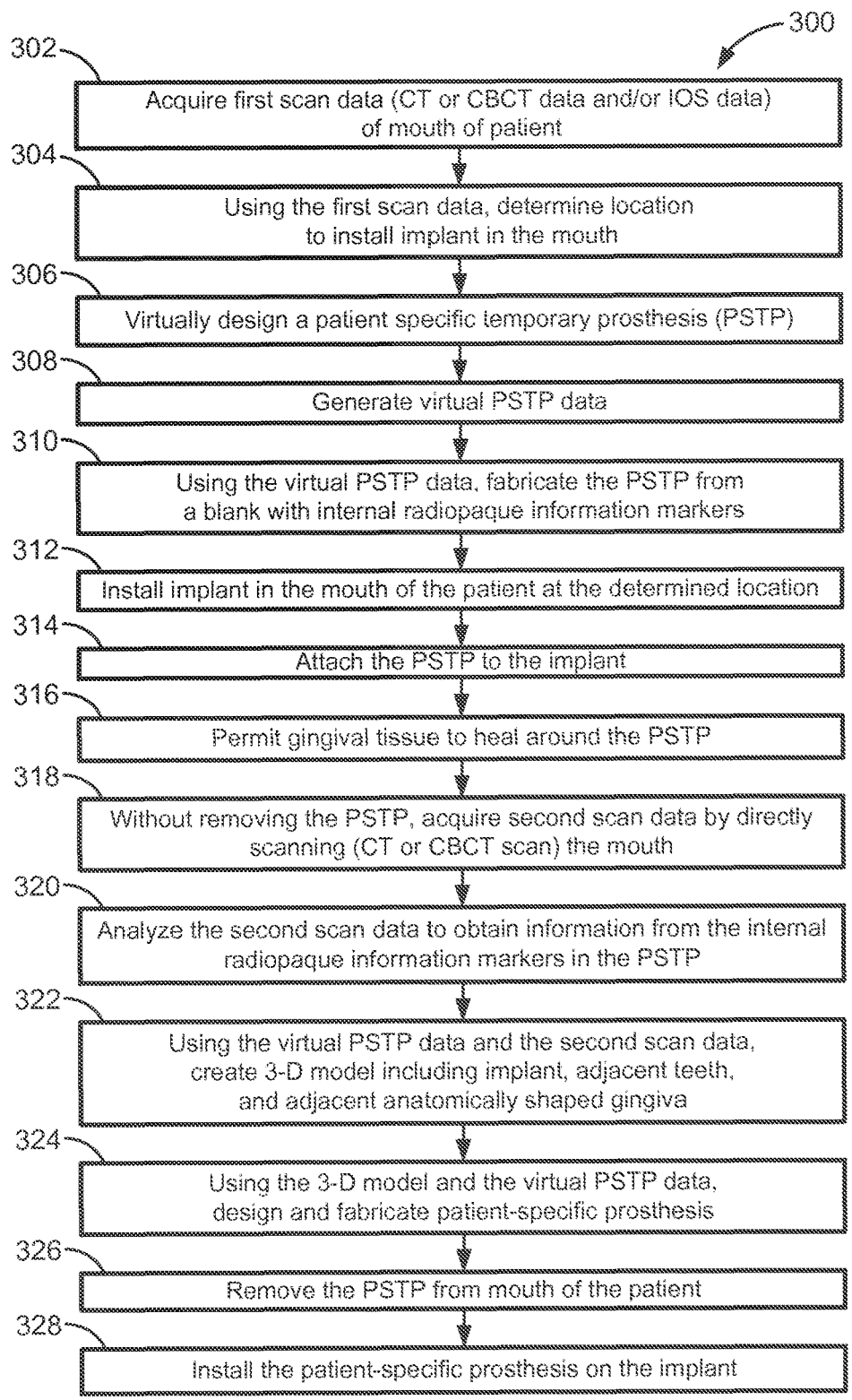
FIG. 11 is a flow chart of a method for manufacturing a permanent tooth prosthesis according to some aspects of the present disclosure.

Now referring to FIG. 11, a method 300 of manufacturing a permanent patient-specific prosthesis (e.g., a final prosthesis) for attachment to a dental implant 60 installed in a mouth of a patient is described in reference to a flow chart. Initially, first scan data is acquired of at least a portion of a mouth of a patient (302). The first scan data can include CT scan data and/or IOS scan data. The first scan data is used during surgical planning to determine a location for installation of a dental implant in the mouth of the patient (304). Based on the determined location of for the dental implant (which is to be installed surgically in the mouth of the patient), an attachment member (e.g., attachment member 10a, 10b, 10c) with internal radiopaque information markers 50, such as, a PSTP-type attachment member, is virtually designed using design software to create a virtual three-dimensional model of a virtual PSTP. Examples of such software used to create a virtual three-dimensional model of a virtual PSTP include CAD Design Software available from 3Shape A/S located in Copenhagen, Denmark; DentalCAD available from exocad GmbH in Darmstadt, Germany; and DentCAD available from Delcam plc in Birmingham, United Kingdom.

Virtual PSTP data is generated (308) from the virtually designed PSTP. The virtual PSTP data can be sent as a set of instructions to a milling machine and/or a rapid-prototype machine to manufacture an actual PSTP (310). The actual PSTP can be one of the attachment members 10a, 10b, and 10c, or a different attachment member/PSTP. The actual PSTP is substantially an exact replica of the virtual three-dimensional model of the virtual PSTP designed using the design software. In some implementations, the actual PSTP is fabricated on a milling machine from a blank attachment member 85 (FIG. 5) with internal radiopaque information markers 50.

The dental implant 60 is then installed into the mouth of a patient at the predetermined location (312). Then the fabricated PSTP with the internal radiopaque information markers 50 is attached to the dental implant 60 (314). In some implementations, the PSTP is attached to the dental implant 60 in a non-rotational fashion (e.g., using complementary non-rotational structures 14, 62) and held in place using a screw fastener (e.g., screw 15). After the PSTP is attached to the dental implant 60 (314), the patient's gingival tissue is permitted to heal around the PSTP (316). The gingival tissue generally heals in a shape with an emergence contour profile that corresponds to the external contours (e.g., exterior side surface 34) of the PSTP abutting the gingival tissue.

After the gingival tissue is permitted to heal (316) for a predetermined amount of time (e.g., a day, two weeks, a month, three months, six months, a year, etc.), without removing the PSTP, the mouth of the patient is scanned with a CT scanner (e.g., CBCT scanner) to obtain/acquire second scan data (318) of at least a portion of the mouth of the patient including the PSTP therein, adjacent teeth, adjacent gingival tissue, etc. That is, the CT scan occurs without having to remove the PSTP from the patient's mouth. Then the second scan data (i.e., CT scan data) is analyzed to obtain information from the internal radiopaque information markers 50 (320) in the same or similar fashion as described above in connection with element (110) in FIG. 9.

Then, the virtual PSTP data and/or the second scan data is used to create and/or display (e.g., on a computer monitor display) a three-dimensional model of at least a portion of the patient's mouth (322) including, for example, a virtual three-dimensional model of a dental implant, a virtual three-dimensional model of adjacent teeth, and a virtual three-dimensional model of adjacent gingival tissue (e.g., having an anatomical shape and a gingival margin), where these structures are positioned in a manner corresponding to the real (i.e., non-virtual) structures in the patient's mouth. In some implementations, only the second scan data is used to create the three-dimensional model of the at least a portion of the patient's mouth.

Then, using the three-dimensional model of the at least a portion of the patients mouth and using the virtual PSTP data, a patient-specific prosthesis is designed and then fabricated (324). With the patient-specific prosthesis fabricated (324), the PSTP is removed from the mouth of the patient (326) and the patient-specific prosthesis (e.g., patient-specific abutment and patient-specific crown) is attached to the dental implant 60 (328).

The portion of the of the attachment members 10a-10e of the present disclosure that contains the set of radiopaque information markers 50 (e.g., the body 30, 30a/30b, the cap portion 11a) can be made of a wide variety of materials, such as, for example, poly-ether-ether-ketone (PEEK), polycarbonate, polymethylmethacrylate (PMMA), polyoxymethylene, polytetrafluoroethylene (PTFE), or any combination thereof. The radiopaque information markers 50 of the present disclosure can be made of a wide variety of materials, such as, for example, steel (e.g., stainless steel), cobalt-chromium alloys, titanium and its alloys, agnesium and its alloys, nitinol and its alloys.

While the attachment members of the present disclosure are described as and illustrated as including a screw 15 and a screw access bore 20 to couple the attachment member to the dental implant 60, such features can be eliminated and replaced with, for example, a snap-in feature that couples the attachment member to the dental implant 60 without a screw and/or a screw access hole.

Alternatively to the methods of fabrication of the attachment members of the present disclosure described above, in some alternative implementations, a clinician manually positions the radiopaque information markers 50 into the body 30. For example, an attachment member can be manually shaped/fabricated from a moldable/malleable material (e.g., acrylic). During the formation of the attachment member (or at least a portion of the attachment member, e.g., the body 30) when the body is still soft (e.g., not hardened), the clinician presses a number of the radiopaque information markers 50 into the body 30 such that the radiopaque information markers 50 are internal to the body 30 of the attachment member. In such alternatives, where the radiopaque information markers 50 are manually positioned in the body 30 (e.g., not positioned at a known location relative to the screw access hole), the above described methods of developing and fabricating patient-specific prostheses differs in that a further step of scanning (i.e., a CT scan) the manually formed attachment member outside of the mouth is necessary to capture the relationship of the manually positioned radiopaque information markers 50 and the central axis of the screw access hole and/or the location of the coordinate system for the dental implant installed in the mouth of the patient. In some such implementations, the manually formed attachment member with the manually positioned radiopaque information markers 50 is attached to a fixture for the CT scanning outside of the mouth. The information obtained from the scan of the manually formed attachment member outside of the mouth of the patient is used later on when CT scanning the manually formed attachment member in the mouth of the patient to locate the dental implant and/or the gingival margin after a healing period.

While the present disclosure has been described with reference to one or more particular embodiments and implementations, those skilled in the art will recognize that many changes may be made thereto without departing from the spirit and scope of the present disclosure. Each of these embodiments and implementations and obvious variations thereof is contemplated as falling within the spirit and scope of the present disclosure, which is set forth in the claims that follow.

What is claimed is:

1. An attachment member for mating with a dental implant, comprising:
   a non-rotational structure configured to mate with a corresponding non-rotational feature of the dental implant, the non-rotational structure defining a first screw access through bore;
   a body extending from the non-rotational structure and defining a second screw access through bore extending though the entire body, the body having a first body portion and a second body portion, the first body portion having a first top surface defining at least one first recess, the second body portion having a bottom surface defining at least one second recess that corresponds to the at least one first recess in the first body portion to form a radiopaque marker cavity, the second body portion having an exterior top surface that is exposed through the gingival tissue;
   at least one radiopaque information marker located within the radiopaque marker cavity internal to an exterior side surface of the first and second body portions and the exterior top surface of the second body portion, the at least one radiopaque information marker indicating information regarding the dental implant that is revealed in response to a scan from a computerized tomography (CT) scanner; and
   a screw configured to extend through the first screw access through bore and the second screw access through bore to couple the non-rotational structure and the body to the dental implant.

2. The attachment member of claim 1, wherein the at least one radiopaque information marker is made from a first material having a first level of opacity and the rest of the body is made from a second material having a second level of opacity that is different than the first level of opacity.

3. The attachment member of claim 2, wherein the non-rotational structure is made from a third material having a third level of opacity that is different than the first level of opacity.

4. The attachment member of claim 1, wherein the at least one radiopaque information marker includes three radiopaque information markers, each of the three radiopaque information markers having a spherical shape.

5. The attachment member of claim 4, wherein a diameter of each of the three radiopaque information markers is the same.

6. The attachment member of claim 4, wherein each of the three radiopaque information markers is positioned equidistantly from a central axis of the second screw access through bore.

7. The attachment member of claim 6, wherein a center of each of the three radiopaque information markers is located on a plane that is perpendicular to the central axis of the second screw access through bore.

8. The attachment member of claim 7, wherein the plane is parallel to a second plane including a seating surface of the attachment member.

9. The attachment member of claim 1, wherein at least a portion of the body has a generally cylindrical shape.

10. The attachment member of claim 1, wherein the at least one radiopaque information marker is completely internal to the body such that the at least one radiopaque information marker is not visible.

11. The attachment member of claim 1, wherein in response to the scan from the CT scanner, the at least one radiopaque information marker is configured to be virtually segmented from the rest of the body.

12. The attachment member of claim 1, wherein the non-rotational structure is a portion of an insert and the body is a cap that is configured to couple with the insert in a removable snap-fit fashion.

13. The attachment member of claim 12, wherein the insert is made from metal and the body is made from ceramic, acrylic, porcelain, plastic, or any combination thereof.

* * * * *